(12) United States Patent
Lu et al.

(10) Patent No.: US 7,670,836 B2
(45) Date of Patent: Mar. 2, 2010

(54) **ANTIMICROBIAL PEPTIDE ISOLATED FROM *PENAEUS MONODON***

(75) Inventors: Jenn-Kan Lu, Keelung (TW); Jen-Leih Wu, Taipei (TW); Tze-Ting Chiou, Keelung (TW)

(73) Assignee: Academia Sinica (TW)

( * ) Notice: Subject to any disclaimer, the term of this patent is extended or adjusted under 35 U.S.C. 154(b) by 132 days.

(21) Appl. No.: 11/806,234

(22) Filed: May 30, 2007

(65) Prior Publication Data
US 2008/0032385 A1     Feb. 7, 2008

Related U.S. Application Data

(62) Division of application No. 10/842,005, filed on May 10, 2004, now abandoned.

(60) Provisional application No. 60/470,847, filed on May 16, 2003.

(51) Int. Cl.
*C07H 17/00* (2006.01)
*C07K 14/00* (2006.01)

(52) U.S. Cl. .................... 435/320.1; 536/23.1; 530/350

(58) Field of Classification Search ..................... None
See application file for complete search history.

(56) References Cited

U.S. PATENT DOCUMENTS 6,642,203 B1   11/2003   Destoumieux et al.

OTHER PUBLICATIONS

Tassanakajorn et al. 2001; Accession No. BI784441.*
Tassanakajorn et al. 2001; Accession No. BI784459.*
Premruethai Supungul et al., "Identification of Immune-Related Genes In Hemocytes Of Black Tiger Shrimp (*Peaeus monodon*)", Marine Biotechnology vol. 4, 2002, pp. 487-494.
D. Destoumieux, "Penaeidins, a family of antimicrobial peptides from penaeid shrimp (Crustacea, Decapoda)", Cell. Mol. Life Sci. 57, 2000, pp. 1260-1271.
Delphine Destoumieux et al., "Recombinant expression and range of activity of penaeidins, antimicrobial peptides from penaeid shrimp", Eur. J. Biochem. 266, 1999, pp. 335-346.
Michael Zasloff, "Antimicrobial peptides of multicellular organisms", Nature, vol. 415, Jan. 24, 2002, www.nature.com, pp. 389-395.
Tetsuya Suetake et al., "Chitin-binding Proteins in Invertebrates and Plants Comprise a Common Chitin-binding Structural Motif", The Journal of Biological Chemistry, vol. 275, No. 24, Issue of Jun. 16, pp. 17929-17932, 2000.
Philippe Bulet et al, "Anti-microbial peptides: from invertebrates to vertebrates", Immunological Reviews 2004, vol. 198: pp. 169-184.
Karin van de Braak, "Haemocytic defence in black tiger shrimp (*Penaeus monodon*)", PhD thesis, Wageningen University-with ref.—with summary in Dutch, ISBN 90-5808-651-8, C.B.T. van de Braak, 2002, Wageningen Institute of Animal Sciences, PO Box 338, 6700 AH Wageningen, the Netherlands.

* cited by examiner

*Primary Examiner*—Karen Cochrane Carlson
(74) *Attorney, Agent, or Firm*—Andrews Kurth, LLP

(57) ABSTRACT

The present invention provides an antimicrobial peptide, monodoncin, which is isolated and purified from *Penaeus monodon* and is capable of being mass produced by molecular cloning techniques in a heterologous expression system, such as yeast. Monodoncin demonstrates a wide-range of bacteriostatic and bactericidal effects on G(−) and G(+) bacteria as well as fungicidal activities, and can be used in combination with conventional antibiotics as "cocktail therapy" to improve the therapeutic effects of the conventional antibiotics.

8 Claims, 12 Drawing Sheets

Figure 1 (A)

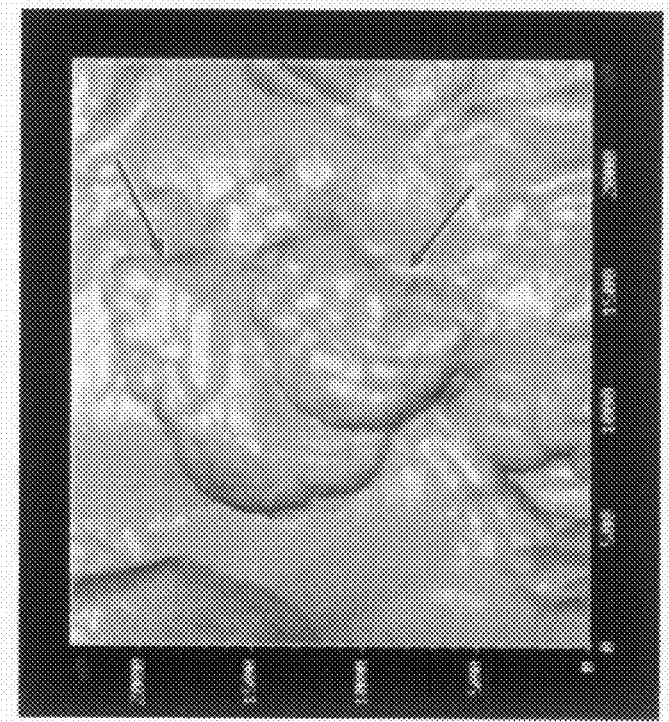
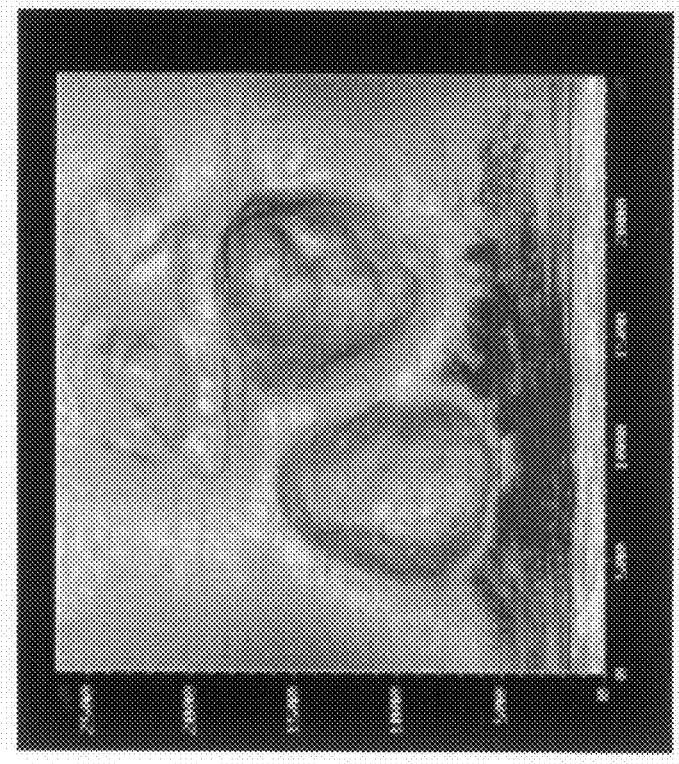
Figure 7

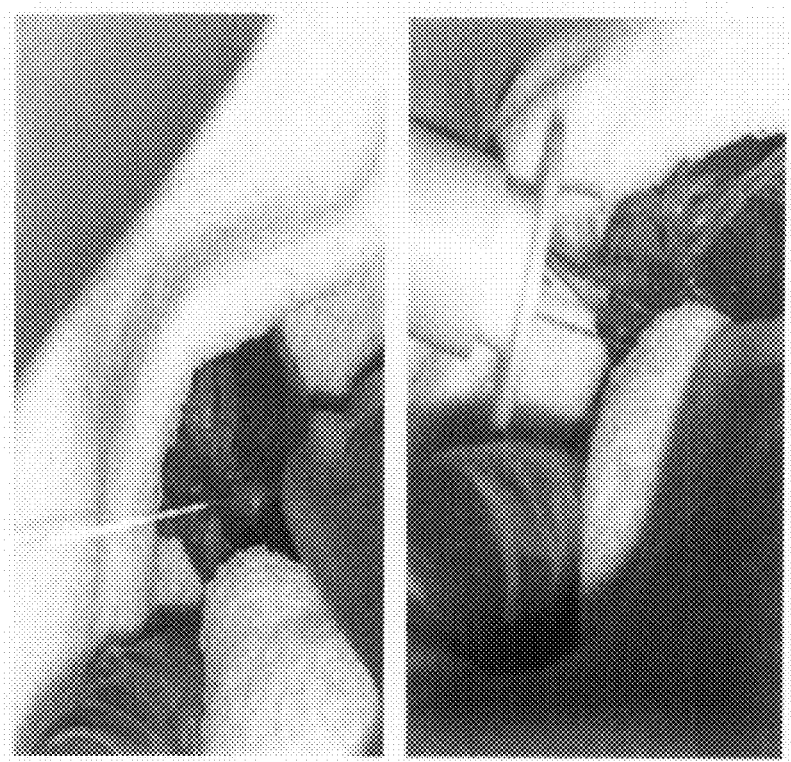
Figure 10 (B)

US 7,670,836 B2

ANTIMICROBIAL PEPTIDE ISOLATED FROM *PENAEUS MONODON*

RELATED APPLICATION

This application is a divisional application of U.S. application Ser. No. 10/842,005, filed May 10, 2004, now abandoned, which claims priority of U.S. provisional application 60/470,847 filed on May 16, 2003, contents of which are incorporated herein by reference.

FIELD OF THE INVENTION

The present invention relates to a novel antimicrobial peptide (AMP), monodoncin, which is isolated and purified from the black tiger shrimp (*Penaeus monodon*), preferably from the hemocytes of *Penaeus monodon*, and can be overexpressed in a heterologous expression system, such as yeast, by molecular cloning techniques. Monodoncin demonstrates a wide-range of bacteriostatic and bactericidal effects on gram (−) and gram (+) bacteria, as well as fungicidal activities, and can be used in combination with conventional antibiotics as "cocktail therapy" to improve the therapeutic effects of the conventional antibiotics.

BACKGROUND OF THE INVENTION

The development of antimicrobial agents led to a significant decrease in morbidity and mortality from infectious diseases in this century. This accomplishment was largely due to the widespread use of the major classes of antibiotics, such as the sulfonamides, penicillins, cephalosporins, aminoglycosides, and tetracyclines (Goodman et al., "The Pharmacological Basis of Therapeutics", Macmillan Publishing, New York, 1985). However, in recent years, the trend in reducing infectious disease mortality has been threatened by the emergence of resistant strains of microorganisms that are no longer susceptible to the currently available antimicrobial agents. As a result, maintenance of public health requires that new antimicrobial agents be developed to counter these emerging resistant strains in order to prevent the diseases that have previously considered to be under control from reemerging.

Biologically active peptides, such as antimicrobial peptides (hereinafter "AMPs), have little chance to develop resistance because the antimicrobial peptides show activity by a mechanism that is totally different from that of the conventional antibiotics. The AMPs are the biophylaxis systems of the species which act to defend or protect itself from the infection by virus or bacteria.

AMPs are low molecular weight natural peptides that exhibit antimicrobial activity. They are part of the innate immune response of plants, invertebrates and vertebrates. Different AMPs have been reported to be isolated from natural sources since 1930s. For example, in 1939 Dubos demonstrated that a soil *bacillus*, subsequently identified as *B. brevis*, produced substances that could prevent pneumococcal infections in mice. Subsequently, Hotchkiss and Dubos purified two substances composed of amino acids and one of these, gramicidin, became available as a therapeutic agent. Subsequent studies on antimicrobial peptides have identified many active agents (Moberg and Cohn (eds), (1990), "Launching the Antibiotic Era. Personal accounts of the discovery and use of the first antibiotics." Rockefeller University Press, New York).

The variety and diversity of the AMPs have been expanding. Cationic peptides are the most widespread form of AMPs, while anionic peptides, aromatic dipeptides, processed forms of oxygen-binding proteins, and processed forms of natural structural and functional proteins have all been reported. In spite of the astonishing diversity in structure and chemical nature among the AMPs, they all present antimicrobial activity. AMPs participate in host defense reactions against invading microorganisms such as bacteria, fungi, parasites, and enveloped virus.

To date, the AMPs are temporarily grouped into four distinct families based on biochemical characteristics:

(I) Linear cationic basic peptides forming amphipathic α-helices, such as the cecropins, the first antimicrobial peptide isolated from insect hemolymph (Boman and Hultmark, (1987), *Ann. Rev. Microbiol.* 41:103-126); and the magainins found in the skin of *Xenopus laevis* (Zasloff, (1987), *Proc. Natl. Acad. Sci. USA,* 84:5449-5453).

(II) Peptides with one to six intramolecular disulfide linkages, such as the defensins (Hoffmann and Hetru, (1992), *Immunol. Today* 13:411-415); antifungal peptides from *Drosophila*, drosomycin (Fehlbaum et al., (1994), *J. Biol. Chem.* 269:33159-33163); thanatin from Podisus (Fehlbaum et al., (1996), Proc. Natl. Acad. Sci., USA, 93:1221-1225); tachyplesin, big defensin, and tachycitin from limulus (Nakamura et al., (1988), *J. Biol. Chem.* 263:16709-16713); and other cysteine-rich antimicrobial peptides isolated from a scorpion (Ehret-Sabatier et al., (1996), *J. Biol. Chem.* 271: 29537-29544) and a bivalve mollusk (Charlet et al., (1996), *J. Biol. Chem.* 272:28398-28406).

(III) Proline-rich peptides, such as apidaecins and abaecins from Hymenoptera (Casteels et al., (1990), *Eur. J. Biochem.* 187:381-386); and drosocin from *Drosophila hemolymph* (Bulet et al., (1993), *J. Biol. Chem.* 268:14893-14897).

(IV) Glycine-rich antimicrobial peptides or polypeptides (9-30 kDa), such as the attacins (Hultmark, et al., (1983), *EMBO J.* 2:571-576), diptericin (Dimarcq et al., (1988), Eur. J. Biochem. 171:17-22), and sarcotoxins (Kanai and Natori, (1990), Mol. Cell. Biol. 10(12): 6114-22).

Although AMPs have been discovered in a variety of animals and plants, very few findings of AMPs in the Crustaceans have been reported, probably due primarily to their unique immune system. Among the Crustaceans, penaeid shrimp represents one of the fastest growing Crustaceans in the world. Penaeid shrimp belong to the largest phylum in the animal kingdom, the Arthropoda. This group of animals is characterized by the presence of paired appendages and a protective cuticle or exoskeleton that covers the whole animal. The subphylum Crustacea is made up of 42,000, predominantly aquatic, species, that belong to 10 classes. Within the class Malacostraca, shrimp, together with crayfish, lobsters and crabs, belong to the order Decapoda.

Tiger shrimp (*Penaeus monodon Fabricius*), also known as black tiger shrimp, black tiger prawn, giant tiger shrimp, is one of the most important cultivated shrimp species in the marine shrimp aquaculture industry around the world. Tiger shrimp belongs to the Family of Penaeidae Rafinesque, Genus of *Penaeus Fabricius*, Subgenus of *Penaeus*, and Species *monodon*. Other important cultured penaeid shrimp species include Pacific white shrimp (*P. vannamei*), kuruma shrimp (*P. japonicus*), blue shrimp (*P. stylirostris*), and Chinese white shrimp (*P. chinensis*). World shrimp production is dominated by *P. monodon*, which accounted for more than 50% of the production in 1999. Tiger shrimp is widely distributed throughout the greater part of the Indo-Pacific region, ranging northward to Japan and Taiwan, eastward to Tahiti, southward to Australia, and westward to Africa.

The giant black tiger shrimp (*P. monodon*) derived its name from the huge size and banded tail, providing a tiger-striped appearance to this species. It is by far the largest, reaching 330 mm or more in body length, and exhibits the highest growth rate, of all cultured penaeids. (Lee and Wickins, (1992), Blackwell Scientific Publications; The University press, Cambridge, 392 pp). *P. monodon* can reach a market size up to 25-30 g within 3-4 months after postlarvae stocking in culture ponds and tolerates a wide range of salinities. Although *P. monodon* was normally considered as exceptionally tough, the rapid growth and intensification of its culture industry generated crowding and increased environmental degradation, which made the animals more susceptible for diseases.

The shrimp aquaculture industry has suffered huge economic loss due to diseases, which mainly caused by viruses and bacteria, and to a lesser extent, rickettsiae, fungi, and parasites. For example, the white spot syndrome virus (WSSV) has had a great impact on shrimp culture and at present still causes major problem in *P. monodon*. Other important viruses include infectious hypodermal and haematopoietic necrosis (IHHN) virus, hepatopancreatic parvovirus (HPV), baculoviral midgut gland necrosis (BMN) virus, baculovirus penaei (BP), yellow head virus (YHV), monodon baculovirus (MBV), lymphoid organ vacuolisation virus (LOVV) and Taura syndrome virus. Viral diseases are often accompanied by bacterial infestations. However, only a small number of bacterial species have been diagnosed as infectious agents in penaeid shrimp. *Vibrio* spp. are by far the major bacterial pathogens and can cause severe mortality, particularly in hatcheries. Vibriosis is often considered to be a secondary (opportunistic) infection, which usually occurs when shrimp are weakened. Primary pathogens can kill even when other environmental factors are adequate, whereas opportunistic pathogens are normally present in the natural environment of the host and only kill when other physiological or environmental factors are poor. However, the differences in effects between primary pathogens, such as the WSSV, and secondary pathogens, such as *Vibrio* spp., are marginal, primarily due to lack of basic knowledge of the interaction between the pathogens of cultivated shrimp and the reaction of the hosts. In fact, the transmission of diseases in an intensive shrimp culture environment is extremely easy, because of the dense culture conditions. Thus, losses of cultivated penaeid shrimp due to diseases, whether slow continuous attrition or sudden catastrophic epizootics, are familiar problems that confront the aquaculture sector.

So far, only a few researches on AMPs have been performed in crustacean. For example, penaeidins, a family of AMPs from the white shrimp (*Penaeid vannamei*), have been isolated. (Destoumieux et al., (2000), *CMLS, Cell. Mol. Life. Sci.* 57:1260-1271). However, the AMPs of the tiger shrimp (*Penaeid Monodon*) remain largely unknown.

In the invention to be presented in the following sections, a novel AMP isolated from *P. monodon*, monodoncin, is described. This AMP has a wide-range of antimicrobial activity, which is particularly important to diseases control to ensure the long term survival of not only penaeid shrimp, but also other aquatic species as well as humans and domestic animals, such as chicken and swine. The investigation of this AMP further provides insights with regard to the understanding of the innate immune system of crustaceans.

SUMMARY OF THE INVENTION

The present invention provides an antimicrobial peptide (AMP) having an amino acid sequence of SEQ ID NO:1 or a fragment thereof. The AMP is isolated and purified from the hemocytes of tiger shrimp (*Penaeus monodon*). The same AMP can also be found in other tiger shrimp tissues, such as gill, intestine, eyestalk, hepatopancreas, and muscle, although the highest expression level is in the hemocytes.

The mature peptide, which is called "monodoncin", contains 55 amino acid residues (from residue 20-glutamine to residue 74-glycine), and have a molecular weight of about 5 to 8 kDa. It is composed of two β-sheets in N-terminus and one α-helix in C-terminus.

The polynucleotide that encodes the monodoncin has the nucleic acid sequence of SEQ ID NO:2 or a fragment thereof (SEQ ID NO:3 or SEQ ID NO: 4). The monodoncin polynucleotide can be inserted into a vector, such as a plasmid or a viral carrier, to form a recombinant construct, and overly expressed in a heterologous expression system, such as in a yeast.

The present invention also provides a composition which comprises the monodoncin and a carrier. The composition is capable of treating a host with bacterial and/or fungal infection. The host can be an aquatic species (such as finfish, crustacean, or molluscus), a domestic animal (such as chicken or swine) or a human. The composition can be used as a pharmaceutical composition for treating patients with bacterial or fungal infection. The pharmaceutical composition can be orally administered or parenterally injected into a human or as a topical preparation for external use.

The monodoncin can be used in a cocktail therapy by combining it with at least a conventional an antibiotic, including, but not limited to, acyclovir, cecropin A, cecropin B, magainin II, pleurocidin, cefaclor, cefadroxil, ciprofloxacin, erythromycin, penicillin, amoxicillin, and tetracycline.

The present invention further comprises a method for inhibiting growth of a microorganism in a host by orally administrating, parenterally injecting, or topically applying the monodoncin-containing pharmaceutical composition to the host. The monodoncin has a wide-spectrum of bacteriostatic and fungistatic effects. Monodoncin also has bactericidal and fungicidal effects.

Finally, the present invention provides a transgenic crustacean, preferably a transgenic penaeid shrimp, and most favorably, a transgenic white shrimp (*Penaeus vannamei*), whose somatic and germ cells contain at least one genomically integrated copy of the recombinant construct containing a nucleic acid sequence encoding the monodoncin. The nucleic acid sequence expresses the monodoncin both spatially and temporally during the development of the crustacean.

BRIEF DESCRIPTION OF THE DRAWINGS

In FIG. 1A, the deduced amino acid sequence of the ORF is shown above the nucleotide sequence of the monodoncin at the top portion of graph. An asterisk in FIG. 1A indicates the stop codon for the monodoncin ORF. The double-headed arrow of FIG. 1A indicates the putative cleavage site by a signal peptidase. The polyadenylation signal is double-underlined. The signal peptide region is indicated by dotted line. The mature peptide regions are indicated by straight lines which are divided by an intron. The nucleotide sequence is boxed by straight lines to reveal the 5' and 3' untranslational region (UTR). The intron region in the sequence encoding for the mature peptide is boxed by dotted lines. FIG. 1B shows a box diagram showing the arrangement of the gene sequence in the monodoncin genomic DNA as 5'-UTR-Exon 1-Intron 1-Exon 2-3'-UTR.

(1997), 272:28398-28406. Only about 46% to 54% of similarity is shown between monodoncin and penaeidin.

Figure 3:
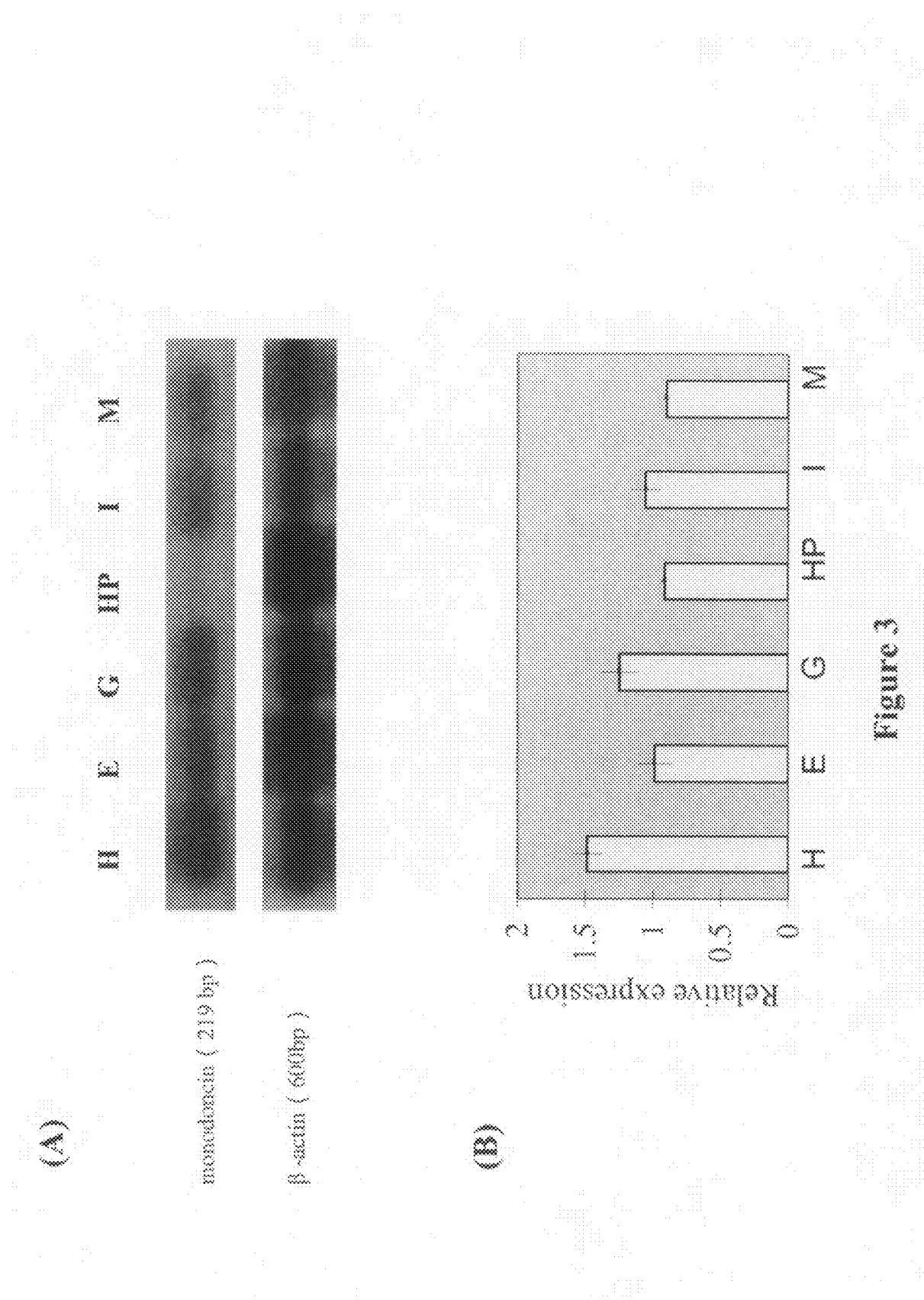

FIG. 3 shows a semi-quantitative analysis of the expression locations of the monodoncin mRNA among various tissues in the tiger shrimp: FIG. 3A shows the result of RT-PCT and southern analysis; FIG. 3B is a diagram showing the relative expression level of the monodoncin RNA in the tissues. H=hemocytes; E=eyestalk; G=gill; HP=hepatopancreas; I=intestine; M=muscle.

Figure 4:
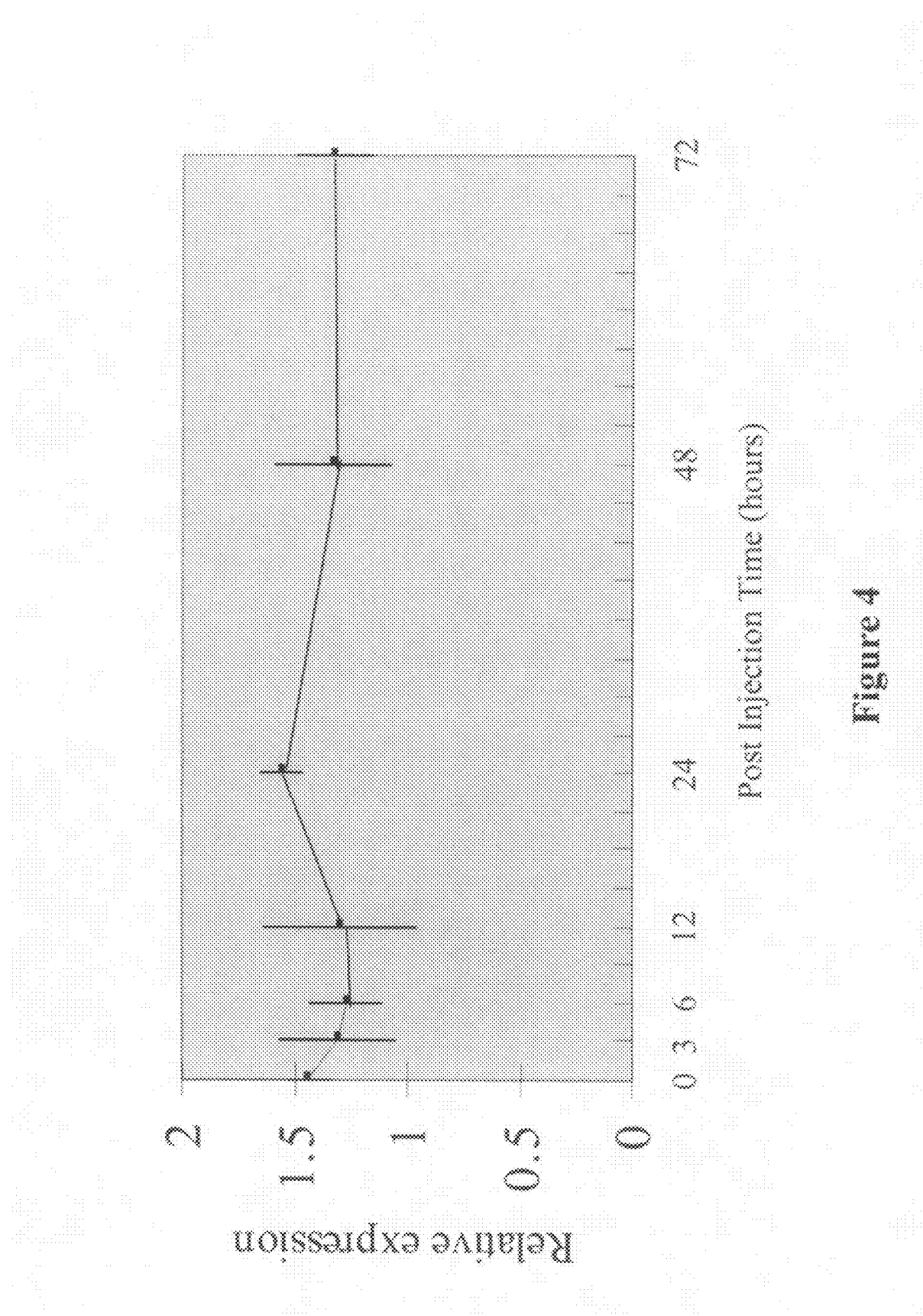

FIG. 4 is a time-course showing the expression of monodoncin in hemocytes between 0 and 72 hours.

Figure 5:
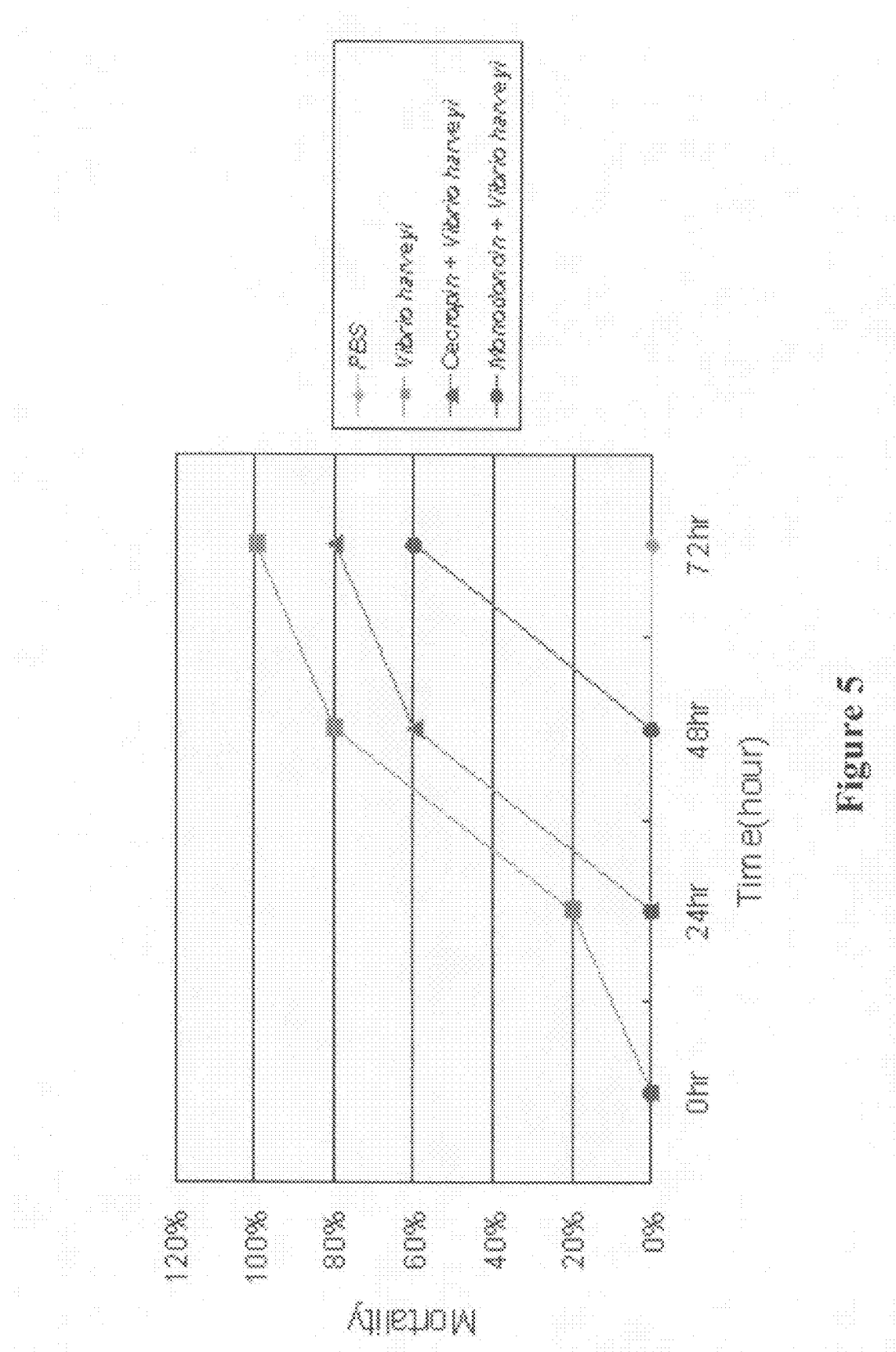

FIG. 5 shows the mortality rates of the tiger shrimp after pathogen. (-◇-): PBS control (negative control); (-■-): *Vibrio harveyi* challenge (positive control); (-▲-): cecropin+ *Vibrio harveyi* (non-monodoncin treatment group); (-●-): monodoncin+*Vibrio harveyi* (monodoncin treatment group). The results show that monodoncin treatment reduced the tiger shrimp mortality by at least 40% after *Vibrio harveyi* challenge.

Figure 6:
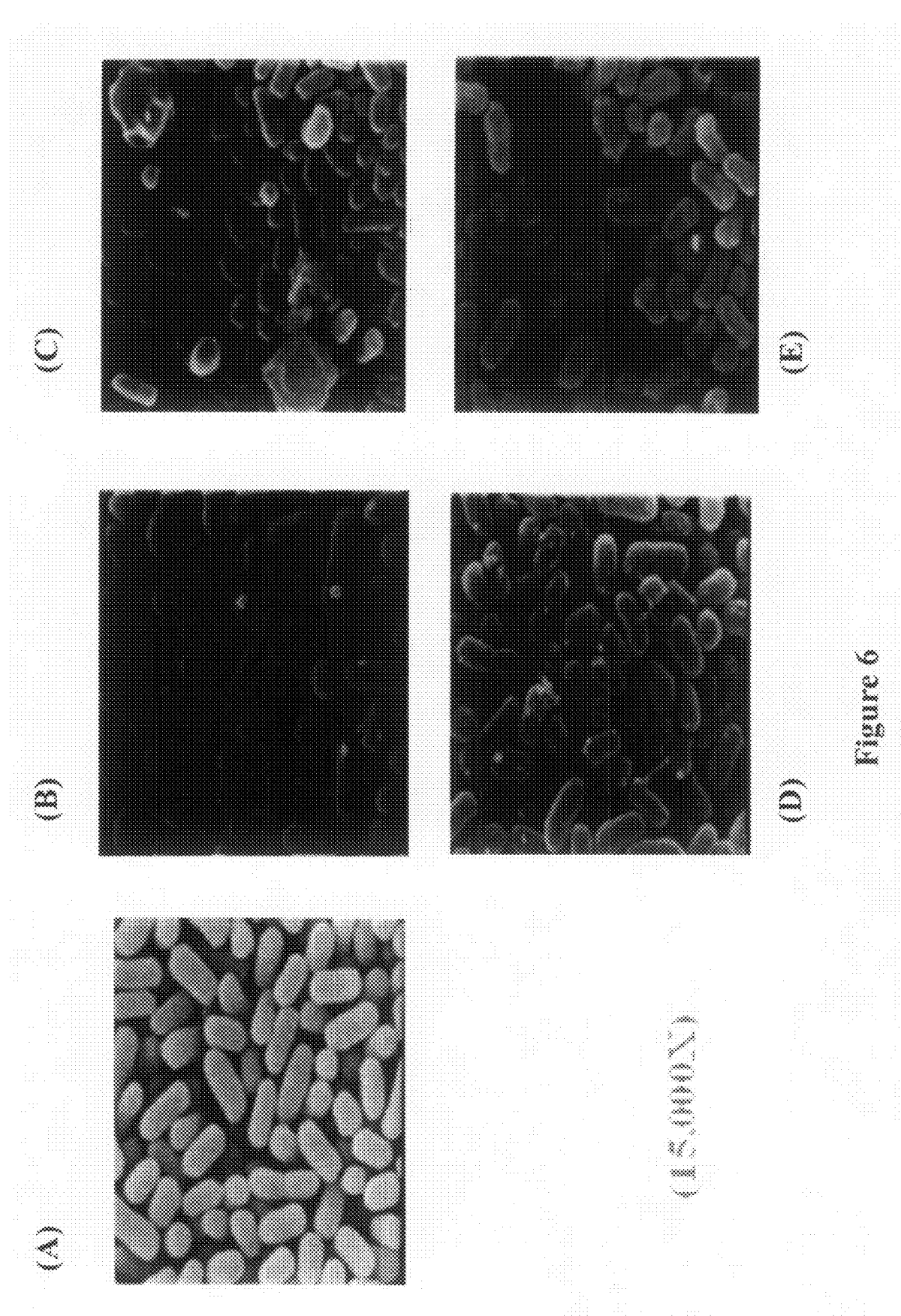

FIG. 6 (A-D) are electron micrographs of *E. coli* viewed under scanning electronic microscopy (SEM) which demonstrates the effect of monodoncin on the cellular membranes of *E. coli* by disrupting and/or forming pores on the membranes and eventually causing the bacterium to lyse. Shown on the graphs were control (with no monodoncin added) (A); (B-C) *E. coli* specimens after 3 hours of monodoncin treatment (10 μM) (bright spots as shown in the photograph were pores formed on the bacterial membranes); (D) *E. coli* specimens after 6 hours of monodoncin treatment (10 μM) (showing disruption and lysis of some microorganisms); and (E) *E. coli* specimens after 12 hours of monodoncin treatment (showing a reduction of total number of microorganisms). (Magification=×15,000).

FIG. 7 (A-B) are electron micrographs of *E. coli* viewed by scanning atomic force microscopy (AFM). (A) Control; and (B) *E. coli* specimens after 10 μM of monodoncin treatment. Arrows shown on the electron micrograph denote the site of a pore on the surface of the cell membrane of the microorganism.

FIG. 8A is an electron micrograph from scanning AFM which shows the surface disruption and formation of a pore on the membrane of *Vibrio harveyi* caused by the interactions between monodoncin and the pathogen (*Vibrio harveyi*). FIG. 8B shows the width of the pore on the surface of the pathogen, which is about 50-60 nm.

Figure 9:
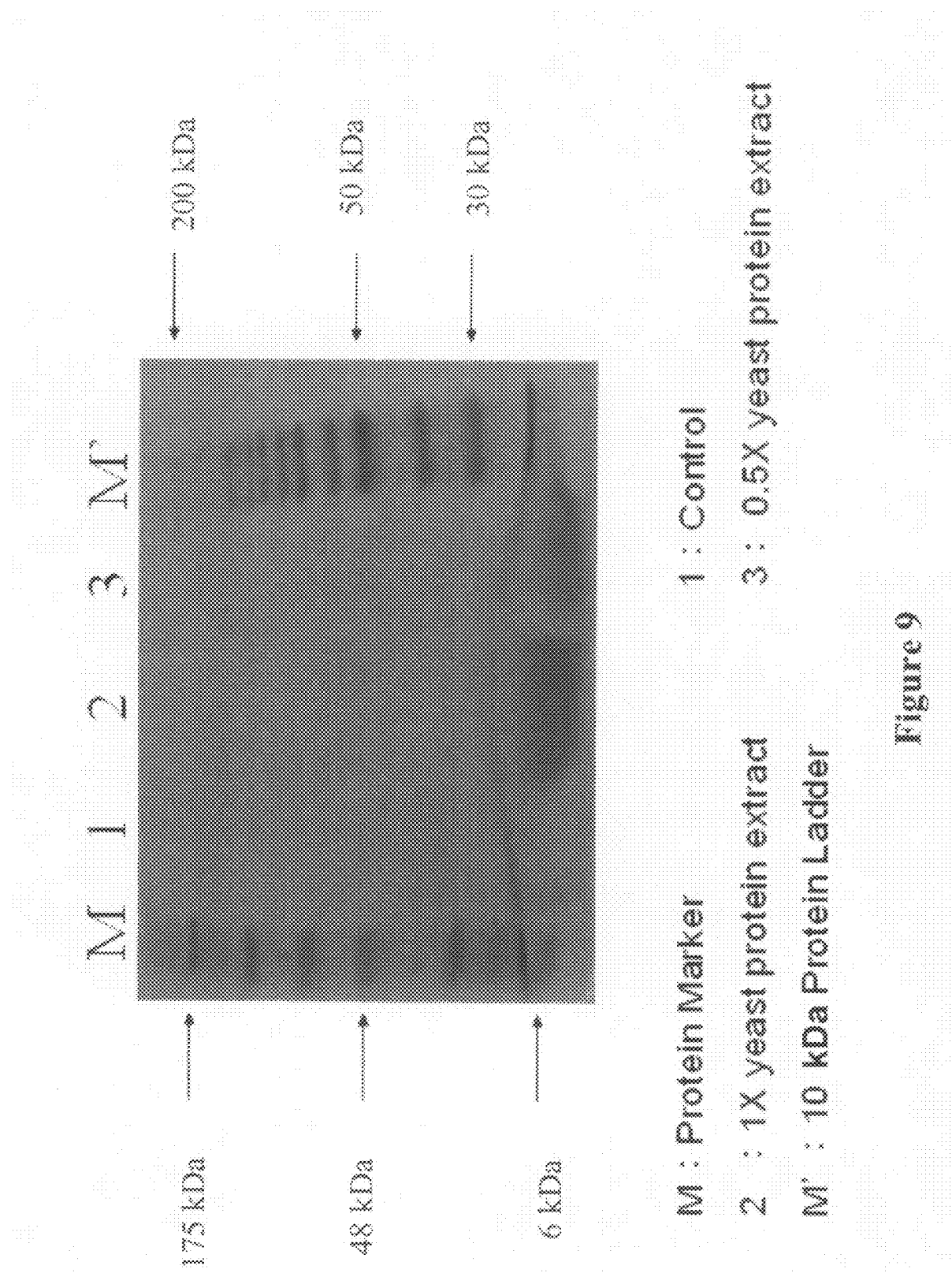

FIG. 9 is a 15% SDS-polyacrylamide gel after electrophoresis demonstrating the expression of monodoncin proteins in yeast. As demonstrated by the SDS-polyacrylamide gel, the monodoncin has a molecular weight of about 5-7 kDa.

FIG. 10 shows an *in vivo* spermatophore-mediated gene transfer (SMGT) of the monodoncin nucleic acid sequence in the thelycum of female tiger shrimp (*Penaeus monodon*) (A) or the spermatophore of male white shrimp (*Lipoppenaeus vannamei*) (B). The gene transfer was conducted using a Baekon 2000 system (Baekon Co., CA) or BTX (San Diego, Calif.), and involved the injection of a transgene solution (containing the monodoncin nucleic acid sequence) into the spermatophores. This was followed by the insertion of BTX 2-Needle array into the spermatophore, and the electroporation at amplitude 1.0~1.5 kv; pulse frequency $2^3$; burst time 0.4 S; cycle number 4; pulse width 90 μS.

DETAILED DESCRIPTION OF THE INVENTION

The Crustaceans lack an adaptive immune system. They rely on a so-called "innate immune system" for responding to and eliminating some potentially noxious microorganisms in an aquatic environment. The Crustaceans have an open circulatory system. They do not have blood and blood cells, instead, they have hemolymph and hemocytes, respectively. The hemocytes play an important and central role in the internal defense of the Crustaceans, especially penaeid shrimp.

The innate immune system of the Crustaceans relies primarily upon the hemolymph cells (also known as hemocytes). Three different cell types of hemocytes have been identified in penaeids. The hyaline cell is the smallest cell type with a high nucleus/cytoplasm ratio and few cytoplasmic granules. The granular cell is the largest cell type with a relatively smaller nucleus and fully packed with granules. The semi-granular cell is an intermediate between the hyaline and the granular cell. (Le Moullac and Haffner, (2000), Aquaculture, 191:109-119).

The Crustaceans' defense systems mainly based on the activity of the hemocytes, include hemolymph coagulation, encapsulation, phagocytosis, melanization by the prophenoloxidase (proPO) system, complement activation, cell agglutination, active oxygen formation, and antimicrobial action. Among them, hemolymph coagulation, prophenoloxidase-mediated melanization, and cell agglutination are induced by foreign substances such as lipopolysaccharide (LPS), (1,3)-β-D-glucan, proteoglycans, and lipoteichoic acid (LTA), resulting in the precipitation of raiding microbes. Then, the immobilized raiders are killed by antimicrobial substances released from various types of hemocytes.

Characterization of Monodoncin

In the present invention, a novel AMP, monodoncin, has been isolated and purified from the hemocytes of tiger shrimp. Other expression locations of monodoncin include gill, intestine, eyestalk, hepatopancreas, and muscle of the tiger shrimp. Although the highest expression level of monodoncin is in the hemocytes, but this immune response is non-inducible experimentally. After *Vibrio harveyi* challenges, there were no significant changes of expression level of monodoncin mRNA found in the hemocytes.

The amino acid sequence of monodoncin consists of 19 amino acids of a signal peptide preceding the mature peptide and 55 amino acids of the mature peptide. Based on the SDS-polyacrylamide gel electrophoresis analysis (FIG. 9), the molecular weight of the mature monodoncin is about 5 to 8 kDa. It has two β-sheets in N-terminus and one α-helix in C-terminus.

The amino acid sequence of the open reading frame (ORF) containing the monodoncin is shown as SEQ ID NO:1. The amino acid residues 1-Met to 19-Ala represents the signal peptide which is cleaved at 19-Ala and 20-Gln. The mature monodoncin contains the amino acid residues from 20-Gln to 74-Gly, also shown in SEQ ID NO:1. The monodoncin is further characterized by its containing of a proline-rich domain at the N terminus and six cysteines at the C terminus.

The genomic DNA of monodoncin has 1346 bp in length as shown in SEQ ID NO:2 with a poly-A tail from 1347-1363 bp. The full-length cDNA sequence of monodoncin is 225 bp in length (shown as SEQ ID NO:3) with an open reading frame encoding the mature monodoncin of 165 bps in length plus a stop codon (shown as SEQ ID NO:4).

Figure 1:
FIG. 1 shows the monodoncin genomic DNA.
Figure 1A:
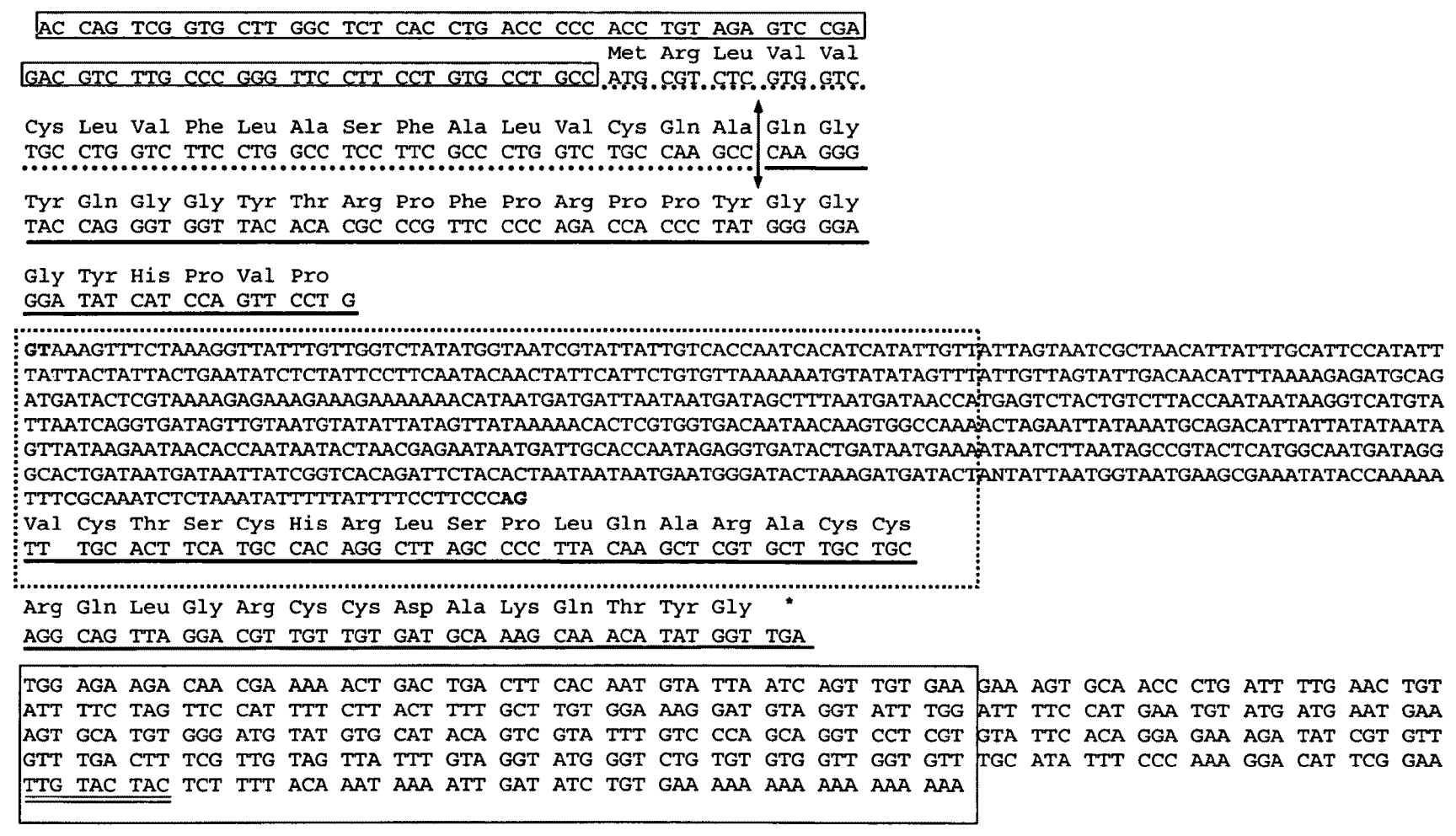
Figure 2:
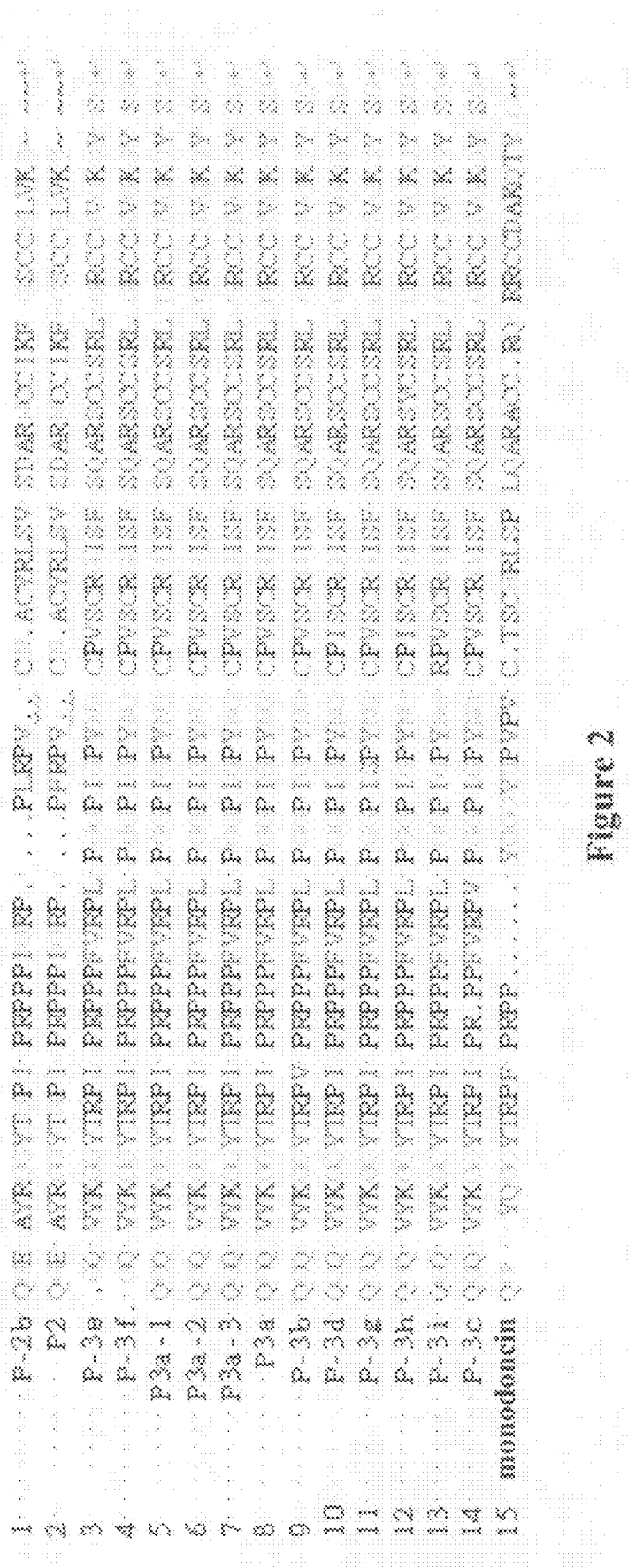
FIG. 2 shows the amino acid sequence comparison between monodoncin and penaeidin-1, penaeidin-2, penaeidin-3a, penaeidin-3b, and penaeidin-3c prepared by the method provided in Destoumieux et al., *J. Biol. Chem.*

As shown in FIGS. 1 and 2, the genomic DNA of monodoncin has a 5' untranslated region (UTR) (80 bps) and Exon 1 (130 bps). It is followed by Intron 1 (680 bps) and Exon 2 (95 bps), with a 3'-UTR (381 bps). The first ORF has a sequence for the signal peptide and a portion of the mature peptide, which is followed by an intron, and Exon 2 (which contains the remaining portion of the ORF with a stop codon). Finally, 3'-UTR contains a poly A signal (base pair 1340 to 1348, TTG TAC TAC in SEQ ID NO 1) and a poly-A tail that end the genome.

The sequence of monodoncin has been compared to other known AMPs. The homology between the full length of monodoncin and penaeidins, a new family of AMPs isolated from white shrimp (*Penaeus vannamei*), is about 24~51% (FIG. 2). Alignment of the monodoncin with published sequences of penaeidins indicates that monodoncin has similar region as the penaeidins. Their signal peptide regions show the highest similarity (91%). Thus, the signal peptide is a highly conserved region within these AMPs at their $NH_2$ termini. The mature peptide sequences have similarity of about 46% to 54%. Monodoncin contains two domains in its overall structure, one proline-rich region at the N terminus and six cysteine residues at the C terminus, which is also the characteristics of the penaeidins.

Monodoncin mRNA has been found in various tissues of the tiger shrimp including hemocytes, eyestalks, gills, hepatopancreas, intestine, and muscles. (FIG. 3). Hemocytes are the defensive phagocytic cells in the shrimp blood circulation. Hemocytes particularly contain high level of monodoncin expression and are useful for isolating monodoncin.

Although the highest expression level of monodoncin is in the hemocytes, experimental result suggests that the immune response is non-inducible, as there are no significant changes of expression level of monodoncin mRNA found in the hemocytes before and after immuno-challenge.

Construction of a Vector for Heterologous Expression of Monodoncin

Monodoncin may be chemically synthesized by the conventional methods of protein synthesis based on the known cDNA sequence or by molecular biology techniques using a host cell system.

SEQ ID NO:4 contains the nucleotide sequence of the matured monodoncin. This sequence, along with the sequence of SEQ ID NO:3, may be used for directly insertion into a vector commonly known in the art, which is then subsequently inserted into a host cell for mass production of monodoncin under appropriate conditions.

Construction of a suitable vector containing the desired nucleic acid sequence employs standard ligation and restriction techniques which are well understood in the art. Isolated plasmids, DNA sequences, or synthesized oligonucleotides are cleaved, tailored, and religated in the form desired. Site specific DNA cleavage is performed by treating with the suitable restriction enzyme (or enzymes) under conditions which are generally understood in the art, and the particulars of which are specified by the manufacturer of these commercially available restriction enzymes.

Large numbers of suitable vectors are known to those of skill in the art, and many are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWL-NEO, pSV2CAT, pOG44, pXT1, pSG (Stratagene) pSVK3, pBPV, pMSG; pSVL (Pharmacia). However, any other plasmid or vector may be used as long as it is replicable and viable in the host.

The techniques for expressing a recombinant vector in a heterologous expression system are well known to persons skilled in the art. Many art-recognized methods are available for introducing polynucleotides, such as the constructs of the invention, into cells. The conventional methods that can be employed, include, e.g., transfection (e.g., mediated by DEAE-Dextran or calcium phosphate precipitation), infection via a viral vector (e.g., retrovirus, adenovirus, adeno-associated virus, lentivirus, pseudotyped retrovirus or poxvirus vectors), injection (e.g., microinjection, electroporation, sonoporation, or a gene gun), liposome delivery (e.g., Lipofectin®, Lipofectamine® (GIBCO-BRL, Inc., Gaithersburg, Md.), Superfect® (Qiagen, Inc. Hilden, Germany) and Transfectam® (Promega Biotec, Inc., Madison, Wis.), or other liposomes developed according to procedures standard in the art), or receptor-mediated uptake and other endocytosis mechanisms.

For the expression of a nucleic acid sequence in vitro, as a means of expression, prokaryotic cells such as *Eschericia coli*, bacilli (e.g., *Bacillus subtilus*) and other enterobacteriacease (e.g., *Salmonella, Serratia*, and various *Psuedomonas* species), and eukaryotic cells such as insect cells (e.g., *Spodoptera frugiperda* Sf9, deposit ATCC CRL 1711), yeasts (e.g., *Saccharomyces cerevisiae* or *Pichia pastoris*), or mammalian cells (e.g., CHO, BHK) have been widely used.

The use of *E. coli* for expression of proteins definitely has some advantages. This is particularly true since the *E. coli* genome has been fully mapped and the microorganism is easy to handle and requires an inexpensive, easy to prepare medium for growth. In addition, *E. coli* secretes protein into the medium, which facilitates the recovery of the protein. However, *E. coli* is a prokaryote which lacks intracellular organelles, such as endoplasmic reticulum and golgi apparatus, that are present in eukaryotes. These intracellular organelles are responsible for modifications of the proteins being produced. Thus, many eukaryotic proteins which can be produced in *E. coli* may be produced in a nonfunctional, unfinished form, since glycosylation or post-translational modifications do not occur. Therefore, in some events, using eukaryotic cells, such as yeast and mammalian cells, as heterologous expression systems for protein production may be deemed more appropriate.

The use of a eukaryotic expression system has certain advantages over a prokaryotic host system. One example of such system is the methanoltrophic *Pichia pastoris*, a eukaryotic yeast. (Cino, J., www.nbsc.com/files/papers/abl_pichia.pdf). *Pichia pastoris* was developed into an expression system by scientists at Salk Institute Biotechnology/Industry Associates (SIBIA) for high-level expression of recombinant proteins. Since its alcohol oxidase promoter was isolated and cloned in 1985 (Cregg, J. M. et al., *Bio/Technology*, 1997; 5: 479-485; Brierley, R. A. et al. *Annals New York Academy of Sciences*, 1992:350-362), *Pichia pastoris* has been developed into an outstanding host system for the production of foreign proteins. Compared to other eukaryotic expression systems, *Pichia* offers many advantages, for example, *Pichia* does not have the endotoxin problem associated with bacteria nor the viral contamination problem of proteins produced in animal cell culture. Furthermore, *P. pastoris* can utilize methanol as a carbon source in the absence of glucose. The *P. pastoris* expression system uses the methanol-induced alcohol oxidase (AOX1) promoter, which controls the gene that codes for the expression of alcohol oxidase. This enzyme catalyzes the first step in the metabolism of methanol. The AOX1 promoter has been characterized and incorporated into a series of *P. pastoris* expression vectors. Since the proteins produced in *P. pastoris* are typically folded correctly and secreted into the medium, the fermentation of genetically engineered *P. pastoris* provides an excellent alternative to *E. coli* expression systems.

The Baculovirus expression vector system (BEVS) is another example of a convenient and versatile eukaryotic system for heterologous gene expression (Luckow & Summers, *Biotechnology* (1988) 6: 47-55). This expression system is one of the easiest and safest eukaryotic systems for recombinant protein production. A number of genes of both prokaryotic and eukaryotic origin have been expressed using this system. A single insect cell line, susceptible to baculovirus infection, can be used to produce an unlimited number of foreign gene products.

The host cells are cultured under conditions such that monodoncin is expressed and recovered from the culture. The monodoncin expressed in the heterologous system can be further isolated and purified by conventional methods which are known to the artisan. There are some fusion protein-producing vectors (such as pET system, pGEX system, pMAL system, pQE system, pRSET system, or pRIT system), which facilitate protein purification. For example, the pET system (or the pQE, the pRSET) contains a nucleic acid sequence that code for a protein tag (e.g., $his_6$). The incorporation of the gene or nucleic acid sequence into the pET system, therefore, allows the polypeptide(s) encoded by the artificially altered gene or nucleic acid sequence to be fused with the protein tag and purified on a metal ($Ni^{2+}$) chelate affinity chromatography (i.e., the MCAC method). The incorporation of the gene or nucleic acid sequence into the pGEX system allows the polypeptide(s) to be co-expressed with a glutathione S-transferase and purified by the glutathione S-transferase affinity chromatography (i.e., the GST method). The incorporation of the gene or nucleic acid sequence into the pMAL system allows the polypeptide(s) to be co-expressed with a maltose binding protein and purified by the maltose binding protein affinity chromatography (i.e., the MBP method). The incorporation of the gene or nucleic acid sequence into the pRIT system allows the polypeptide(s) to be co-expressed with an affinity tail of Protein A, which can be purified by the IgG-Sepharose chromatography (i.e., the IgG-Sepharose method).

In Vivo Gene Transfer of Monodoncin to Other Crustaceans

The monodoncin nucleic acid sequence of *Penaeus monodon* has been successfully cloned into the genome of other species, including, but not limited to, Crustaceans such as white shrimp (*penaeus vannemei*), through spermatopore-mediated gene transfer, which results in forming a transgenic Crustaceans. (FIG. 10). A transgenic Crustaceans is defined as one whose somatic and germ cells contain at least one genomically integrated copy of a recombinant construct including the monodoncin nucleic acid sequence of SEQ ID NO:2 or a fragment thereof, so as to express monodoncin in the recipient species. The transgenic transfer of monodoncin allows the recipient species produce monodoncin, which would greatly decrease the cost for prevention and treatment of diseases caused by the microbes, especially in aquatic species and aquatic farm industry.

Utility of Monodoncin as an Antimicrobial Agent or a Protein Drug

The increased prevalence of disease is contributing to the rising costs of cultured shrimp and marine fish production. Furthermore, bacterial resistance to conventional antibiotics is becoming more widespread. There have been many recent attempts to find effective replacements for use against infections in aquaculture, agriculture and human medicine. Antimicrobial peptides (AMPs) are one largely unexplored group of antimicrobial compounds that is gaining prominence as potential therapeutants. Monodoncin can be widely used as an antimicrobial agent (for bacteria and fungi) in human or throughout the animal kingdom due to its wide-range of bacteriostatic and bactericidal effects as well as fungicidal activities. (See e.g., Tables 1-2 infra). For example, monodoncin can be used as an antimicrobial agent for tiger shrimp and other aquatic species. For another example, monodoncin can be used as antimicrobial agent in domestic animals, such as chicken and swine. For yet another example, monodoncin can be formulated in a pharmaceutical composition for use in human.

The antimicrobial activity of monodoncin is wide-spectrum and non-specific. Monodoncin has demonstrated antimicrobial effects against gram-negative bacteria, gram-positive bacteria, and fungi.

Particularly, monodoncin is effective against the gram-negative (G (−)) bacteria that cause major infections in humans and animals, such as the enteric bacilli and bacteroides. It has also demonstrated high inhibitory activity against G (−) bacteria, including, but not limited to, *Escherichia coli, Vibrio harveyi, Vibrio alginolyticus*, and *Salmonella choleraesuis.*

Monodoncin is also effective against gram-positive (G (+)) bacteria, including, but not limited to, the genus of *Aerococcus*. For examples, monodoncin has demonstrated high inhibitory activity against *Aerococcus viridan*, which is a major species of the aerobic G(+) cocci that causes pathogenic infections in human and animals.

Monodoncin is also effective against fungi, including, but not limited to, the family of Hypocreaceae. For examples, monodoncin has demonstrated high inhibitory activity against the fungi species within the genus of *Fusarium*, one of the most drug-resistant fungi. Monodoncin shows high inhibitory effects against *Fusarium pisi* and *Fusarium oxysporum.*

Based on scanning electron microscopic (SEM) and atomic force microscopic (AFM) observation, the antimicrobial activity of monodoncin comes from its interaction with the microorganisms by disrupting or forming a pore on the membranes of the microorganisms, thus resulting in bacterial lysis. (FIGS. 6-8).

Monodoncin can also be used in connection with other known conventional antibiotics (such as amoxicillin). (Table 3). The combined use of monodoncin and other antibiotics improves the therapeutic effects of the conventional antibiotics, reduces the required dosage of the conventional antibiotics, and showing a synergistical effect on microorganism inhibition. Thus, it can be used as a part of the "cocktail therapy," to more effectively control the wide-spread of bacterial and/or fungal infections.

Additionally, monodoncin can serve medicinal purpose as a protein drug due to its bacteriostatic and bactericidal effects and fungicidal activities in a wide-range of pathogen spectrum. For the purpose of this invention, a protein drug is referred to as a peptide derived from biotechnological origin. It can be derived from r-DNA and hybridoma techniques.

The use of monodoncin as a protein drug can further be accomplished by a mixing monodoncin with a pharmaceutically acceptable carrier. As shown in FIG. 5, monodoncin reduces the mortality rate of *Penaeus monodon* by at least 40%, so that it can be effectively used as a drug for oral administration or parenteral injection.

Additionally, monodoncin is suitable for topical treatment (such as in the form of a solution, a gel, an emugel, a cream, an ointment, a lotion, a transdermal system, an injection fluid, a suspension, or a patch) to be used as bactericidal agent, fungicidal agent, preservative, or surface active agent, to prevent infection of wounds. The contents of these articles are incorporated herein by reference.

Formulations suitable for topical administration include liquid or semi-liquid preparations suitable for penetration through the skin to the site where treatment is required. Examples of liquid preparations include topical solution and drops. Examples of semi-liquid preparations include liniments, lotions, creams, ointment, paste, gel, and emugel. The pharmaceutical ingredients are in general those commonly used and generally recognized by person skilled in the art of pharmaceutical formulation.

The pharmaceutical composition may further contain a moisturizer, such as glycerol, or an oil, such as castor oil or arachis oil. Cream, ointments, or pastes, are semi-solid formulations made by mixing the pharmaceutical with a greasy or non-greasy base. The pharmaceutical composition is in finely-divided or powdered form and may be alone or in a aqueous or non-aqueous solution or suspension. The pharmaceutical composition may be mixed with the greasy or non-greasy base with the aid of suitable machinery. The base may contain hydrocarbons. Examples of the hydrocarbons include, but are not limited to, hard, soft, or liquid paraffin, glycerol, beeswax, a metallic soap, a mucilage, an oil of natural origin (such as almond, corn, arachis, castor or olive oil), wool fat or its derivative, a fatty acid (such as stearic acid or oleic acid), or a combination thereof. The formulation may also contain a surface active agent, such as an anionic, cationic or non-ionic surfactant. Examples of the surfactants include, but are not limited to, sorbitan esters or polyoxyethylene derivatives thereof (such as polyoxyethylene fatty acid esters) and carboxypolymethylene derivatives thereof (such as carbopol).

Suspending agents such as natural gums, cellulose derivatives inorganic materials such as silicaceous silicas, and other ingredients such as lanolin, may also be included. For ointment, polyethylene glycol 540, polyethylene glycol 3350, and propyl glycol may also be used to mixed with the pharmaceutical composition.

A gel or emugel formulation includes any gel forming agent commonly used in the pharmaceutical gel formulations. Examples of gel forming agents are cellulose derivatives such as methyl cellulose, hydroxyethyl cellulose, and carboxymethyl cellulose; vinyl polymers such as polyvinyl alcohols, polyvinyl pyrrolidones; carboxypoly-methylene derivatives such as carbopol. Further gelling agents that can be used for the present invention are pectins and gums (such as gum arabic and tragacanth, alginates, carrageenates, agar and gelatin). The preferred gelling agent is carbopol. Furthermore, the gel or emugel formulation may contain auxiliary agents commonly used in the kind of formulations such as preservatives, antioxidants, stabilizers, colorants, and perfumes.

Monodoncin may be co-administered with other antibiotics, in the so-called cocktail therapy, which may demonstrate synergistic capability for bactericidal and bacteriostatic effects as well as fungicidal activities, while avoiding problems of antibiotic abuse caused by antibiotic-resistant microbes. As shown in Table 3, the co-administration of monodocin and amoxicillin allow reduced amoxicillin dosage or therapeutic alternative for inhibiting pathogen infection in human or animals. The examples of the antibiotics that can be co-administered with monodoncin include, but is not limited to acyclovir, cecropin A, cecropin B, magainin II, pleurocidin, cefaclor, cefadroxil, ciprofloxacin, erythromycin, penicillin, amoxicillin, or tetracycline. For cocktail therapy, the pharmaceutical composition having an effective amount of monodoncin, are mixed with other antibiotics, and administered to the subject.

The following examples are illustrative, but not limiting the scope of the present invention. Reasonable variations, such as those occur to reasonable artisan, can be made herein without departing from the scope of the present invention.

EXAMPLE 1

Obtaining Full Length Monodoncin cDNA

Animal Care and Tissue Collection

Black tiger shrimps weighing about 20±5 g were maintained at 1 ton tanks equipped with air-lift circulating sea water at 28° C. Hemolymph was taken from the ventral sinus of the tiger shrimp located at the base of the first abdominal segment during the inter-molt stage and mixed with an equal volume of anticoagulant Modified Alsever Solution (MAS) (27 mM sodium citrate, 336 mM NaCl, 115 mM glucose, 9 mM EDTA, pH 7). The mixture was directly centrifuged at 800×g for 15 minutes at 4° C. to separate hemocytes from plasma (cell-free hemolymph). Various tissues including eyestalks, gills, hepatopancreas, intestines, and muscles, were dissected and collected after the hemolymph collection.

PCR Analysis and Sequencing of Monodoncin Partial cDNA

The upstream sense primer MP-1 shown as SEQ ID NO: 5 (5'-GTCTGCCAA GCCCAAGGGTAC-3'), and the downstream antisense primer MP-2 shown as SEQ ID NO: 6 (5'-CTGCCTGCAGCAAGCACGAGC-3') were designed and used for PCR cloning. The positions of the primers used for the PCR analysis are indicated by arrows above the genomic sequence for monodoncin gene as in FIG. 1.

Total RNA was extracted from hemocytes of unchallenged black tiger shrimp, using TRIzol reagent (Invitrogen). The first-strand cDNA synthesis was performed from 5 µg total RNA by reverse transcription using Moloney murine leukemia virus reverse transcriptase (Invitrogen) with the oligo $d(T)_{18}$ primer. PCR amplification was performed over 35 cycles according to the following program: melting at 94° C. for 1 min, annealing at 50° C. for 1 min, and elongating at 72° C. for 1 min. The PCR products were cloned into pGEM-T Easy T-overhang Vector System (Promega) and several clones were sequenced.

PCR Analysis and Sequencing of Monodoncin Full-Length cDNA

The mRNA was purified from the total RNA, using Oligotex Mini mRNA Kit (QIAGEN) as instructed. The first-strand cDNA synthesis was performed from 5 µg purified mRNA (by reverse transcription using Moloney murine leukemia virus reverse transcriptase (Invitrogen) with the oligo $d(T)_{18}$ primer.

PCR amplification was performed over 35 cycles according to the following program: melting at 94° C. for 1 min, annealing at 50° C. for 1 min, and elongating at 72° C. for 1 min.

The reaction mixture was stored at −20° C. (QT-cDNA). Thirty-five cycles of PCR were performed on half (10 µl) of the QT-cDNA with the use of MP-1 and MP-2 primers. The temperature profile for the PCR was 94° C. for 1 min, 50° C. for 1 min and 72° C. for 1 min, with the step-cycle programmed on a Hybaid DNA Thermal in 25 µl of 50 mM KCl, 20 mM Tris-HCl (pH8.3), 1.5 mM MgCl, 0.2 mM dNTPs, containing 10 µl of QT-cDNA and 200 pmol of each primer. The PCR product was analyzed by agarose gel electrophoresis and the fragments were eluted by gel extraction (QIAquick gel extraction kit, QIAGEN). The fragments were cloned into the pGEM-T Easy T-overhang Vector System (Promega) and several different clones were sequenced.

Molecular Cloning of Monodoncin Full-Length cDNA by Rapid Amplification of cDNA End (RACE)

Two Primers were Designed on the Basis of the Partial Sequences (141 Bp Fragment) corresponding to the penaeidins. An upstream sense primer, Ps-1 had the sequence 5'-CAGGGTGGTTACACACGCCCGTTCCCC-3' shown as SEQ ID NO:7. A downstream anti-sense primer, Ps-2 had the sequence 5'-GCAGCAAGCACGAGCTTGTAAGGGGCT-3' shown as SEQ ID NO:8.

The 3'-end cDNA amplification was performed by 3'RACE system (Gibco BRL company). First-strand cDNA (Qa-cDNA) was synthesized by Abridged adaptor primer (5'-GGCCACGCGTCGACTAGTACTTTTTTTTTTTTTTTTT-3') as shown with SEQ ID NO: 9. Thirty-five cycles of PCR were performed on half (10 µl) of the Qa-cDNA with the use of Ps-1 and Abridged Universal Amplification Primer (AUAP; 5'-GGCCACGCGTCGAC TAGTAC-3') (as shown in SEQ ID NO:10) primers with the following temperature profile: 94° C. for 1 min, 45° C. for 1 min and 72° C. for 1 min, The resulting PCR of approx. 520 bp was cloned into the pGEM-T-easy vector and sequenced.

The 5'-end cDNA amplification was performed with a Life Technologies 5'RACE system. First-strand cDNA synthesis was performed with Ps-2 primer to give Ps-2-cDNA, which was then tailed with terminal transferase and dCTP to create an abridged primer-binding site [oligo(dC)] on the 3' end of the cDNA. The target cDNA was amplified by nest PCR with the same temperature profile and cycle number as above. The first round PCR was performed with Abridged Anchor Primer (5'-GGCCACGCGTCGACTAGTACGGGII GGGI-IGGGIIG-3', SEQ ID NO:11, provided with the kit) and the anti-sense primer MP-2 (SEQ ID NO:12). The second round of PCR used anti-sense MP-2 primer and AUAP. The amplified product was cloned into the pGEM-T-easy vector and sequenced.

The results were as follows: Initially, the sense primer MP-1: 5'-GAATTCCAAGGGTACCAGGGTGGTTA-CACA-3' (SEQ ID NO:13) and MP2 5'-CGGCCGTCAAC-CATATGTTTGCTTTGC-3' (SEQ ID NO:12) were used on oligo(dT)-primed cDNA to amplify and cloned a 165 bp internal fragment of monodoncin. The full-length cDNA of monodoncin was cloned by 5' and 3'RACE PCR. The full-length fragment was cloned into a pGEM-T-easy vector for DNA sequence determination. The full-length cDNA sequence contained a 222 bp ORF encoding a protein of 74 residues, a 360 bp 3' UTR, a 80 bp 5' UTR and a poly(A) tail. The 3' UTR contains one copy of the mRNA instability consensus sequence ATTTA at position 648 bp of the monodoncin cDNA sequence. A polyadenylated signal site (AATAAA) is also located 12 bp upstream from the poly(A) tail. Translation of the cDNA sequences of the ORF yielded a 19-amino acid signal peptide followed by a 55-amino acid mature peptide. (FIG. 1).

EXAMPLE 2

Expression of Monodoncin

Monodoncin mRNA Expression in Various Tissues of *P. monodon*

Tissue localization of monodoncin mRNA expression in unchallenged animals were examined. Total RNA was extracted from *P. monodon* tissues and hemocytes using Trizol reagent (BRL, Life technologies). The 4 µg total RNA from each tissue or hemocytes of signal shrimp was reverse transcription (RT) PCR by superscript TMII (BRL, Life technologies) and Platinum Taq DNA polymerase. The RT-PCR following conditions were described by BRL, Life technologies. The RT-PCR products were separated by 1.2% agarose gel electrophoresis and transfer to a Nylon membrane and hybridized with partial sequence of monodoncin Dig-labeled probe were quantified by STORM™ system and compared to those obtained with the β-actin specific probe. Mean values at each tissue were used to determine the monodoncin:β-actin signal ratio (p>0.05). The statistical values were calculated by ANOVA system.

To isolate total RNA of hemocyte, eyestalk, gill, muscle, hepatopancrea and intestine by TRIZOL reagent (BRL, Life technologies) and a pair of gene specific primer were designed to used for reveres transcription polymerase chain reaction. The 4 µg of total RNA from various tissues of a single shrimp were analyzed by RT-PCR and then PCR products were separated by 1.2% agarose gel electrophoresis, transfer to a Nylon membrane and hybridized successively with monodoncin Dig-labeled probe were quantified by STORM™ system and compared to those obtained with the β-actin specific probe. Mean values at each tissue were used to determine the monodoncin:β-actin signal ratio (p>0.05). The statistical values were calculated by ANOVA system.

FIG. 3A showed the semi-quantitative RT-PCR and southern transfer analysis of total RNA of monodoncin from various shrimp tissues. The 4 µg of total RNA from various tissues of a single shrimp were analyzed by RT-PCR and then PCR products were separated by 1.2% agarose gel electrophoresis, transferred to a Nylon membrane, hybridized successively with monodoncin Dig-labeled probe were quantified by STORM™ system, and compared to those obtained with the β-actin specific probe. FIG. 3B indicated the relative expression level of monodoncin in various tissues as by the mean values for each tissue of ratio of monodoncin over β-actin signals (p>0.05). As shown in FIGS. 3A and 3B, hemocytes were the main expression site for Monodoncin. The gill, eyestalk, muscle and intestine also expressed monodoncin and their expression levels were lower than hemocytes. The expression of monodoncin in hepatopancrea was the lowest.

Expression of Monodoncin in *Pichia pastoris* and/or *Eshericia coli*

A. A *Pichia* Vector for Multicopy Integration and Secreted Expression

A1: Strains and Media

*Pichia pastoris* was developed into an expression system by scientists at Salk Institute Biotechnology/Industry Associates (SIBIA) for high-level expression of recombinant proteins. The *Pichia pastoris* strain GS115 (Invitrogen life biotechnologies) was used for monodoncin expression in a complete yeast medium (YPD), which contained 1% of yeast extract, 2% of peptone, and 2% of dextrose. Yeast cells were transformed using a lithium acetate method according to Gietz et al., (1992), *Nucleic Acids Res.*, 20: 1425, and transformants were selected on a BMMY medium with kanamycin (Yeast extract 1%, peptone 2%, yeast nitrogen base 1.34%, dextrose 1%, 100 mM potassium phosphate pH 6.0, biotin $4 \times 10^{-5}$%, and methanol 0.5%) supplemented with 0.5% casamino acids lacking uracil. The *Escherichia coli* media and cloning procedures were according to standard methods.

A2: Plasmids

The expression vector, pPIC9K is composed of the 5'AOX1 promoter followed by the sequence of the α-Factor signal peptide and multiple cloning site. The *Pichia pastoris/ E. coli* shuttle vector pPIC9K was described in the catalog no. V175-20 of invitrogen life biotechnologies company.

A3: Amplification of Monodoncin Coding Sequence and Expression Cassette Assembly The sequences encoding the mature monodoncin was amplified from the cDNA clones using Taq DNA polymerase (Roche) with oligonucleotides extended at their 5' end by EcoR I and 3' end by Not I restriction sites. The primer pairs were MP-1 5'-GAATTCCAAGGGTACCAGGGTGGTTACACA-3' (SEQ ID NO:13) and MP-2 5'-CGGCCGTCAACCATATGTTTGCTTTGC-3' (SEQ ID NO:12). The amplified fragments were cloned into pPIC9K, sequenced and subcloned into Top10F'. The fusion was controlled by sequencing and the complete expression cassette was finally subcloned as 177 bp fragments into pPIC9K.

B. A pYC6/CT Vector for Multicopy Integration and Yeast (*Saccharomyces cerevisiae*) Expression system B1: Strains and Media Invitrogen has a wide variety of *S. cerevisiae* expression vectors which can be used with pYES6/CT or pYC6/CT to express and detect multiple proteins in the same cell. Once cloned into pYES6/CT or pYC6/CT, expression of the recombinant protein can be detected using an antibody to the protein itself or to the appropriate epitope. The *S. cerevisiae* strain INVSc1 (Invitrogen life biotechnologies) was used for monodoncin expression. Yeast complete medium was YPD medium (Yeast extract 1%, peptone 2%, glucose 2%). Yeast cells were transformed using the lithium acetate method and transformants were selected on SC medium with blasticidin (Yeast extract 1%, peptone 2%, yeast nitrogen base 0.67%, glucose 2%, 100 mM potassium phosphate pH 6.0, biotin 4×10−5%, galactose 0.5%) supplemented with 0.5% casamino acids lacking uracil. The *Escherichia coli* media and cloning procedures were from standard methods.

B2: Plasmids

The expression vector, pYES6/CT or pYC6/CT are 5.8 kb and 4.5 kb vectors, respectively, designed for inducible expression of recombinant proteins in *Saccharomyces cerevisiae*. Features of the vectors allow dominant selection of yeast transformants and purification and detection of expressed proteins. The vectors contain the following elements: Yeast GAL1 promoter for high level inducible protein expression in yeast by galactose and repression by glucose, multiple cloning site (MCS) with 10 unique sites and two BstX I sites to facilitate in-frame cloning with the C-terminal peptide, C-terminal peptide encoding the V5 epitope and a polyhistidine (6×His) tag for detection and purification of your recombinant fusion protein, 2μ origin for episomal maintenance and high copy replication (pYES6/CT) or CEN6/ARSH4 sequence for non-integrative centromeric maintenance and low copy replication in yeast (pYC6/CT), and blasticidin resistance gene (bsd) for selection in yeast and *E. coli*. The *S. cerevisiae/E. coli* shuttle vector pYES6/CT or pYC6/CT was described in the catalog no. V8257-01 of invitrogen life biotechnologies company.

A3: Amplification of Monodoncin Coding Sequence and Expression Cassette Assembly The sequences encoding the mature monodoncin was amplified from cDNA clones using Taq DNA polymerase (Roche) with oligonucleotides extended at their 5' end by EcoR I and 3' end by Not I restriction sites. The primer pairs were MP-1 5'-GAATTCCAAGGGTACCAGGG TGGTTACACA-3' (SEQ ID NO:13) and MP2 5'-CGGCCGTCAACCATATGTTTGCTTTGC-3' (SEQ ID NO:12). The amplified fragments were cloned into pPIC9K, sequenced and subcloned into Top10F'. The fusion was controlled by sequencing and the complete expression cassette was finally subcloned as 177 bp fragments into pYES6/CT or pYC6/CT.

Preparation of Cell Pellets Resulted from Intracellular and Secreted Expression:

The cell pellets were thawed quickly and place on ice. For a 1 ml sample, 100 μl Breaking Buffer were added to the cell pellets and the cell pellets were resuspended in the Breaking Buffer. An equal volume of acid-washed glass beads (size 0.5 mm) were then added to the resuspended cell pellets, which were vortexed for about 30 seconds to obtain a cell lysate. The cell lysate was then sat on ice for additional 30 seconds. This process was repeated for a total of 8 times. The cell lysate was then centrifuged at maximum speed for about 10 minutes at 4° C. The clear supernatant was transferred to a fresh microcentrifuge tube. About 50 μl of the supernatant was then mixed with 50 μl 2×SDS-PAGE Gel Loading buffer (Sample Buffer). The sample was boiled for 10 minutes prior to loading onto the well (about 10-20 μl per well, which were determined based on the thickness of the gel and the number of wells). The remaining sample was stored at −20° C. for western blots, if necessary. The cell lysate could be stored at −80° C. for further analysis.

Preparation of Supernatant (Secreted Expression Only):

The supernatant of the cells was frozen and thawed and then placed on ice prior to use. About 50 μl of the thawed supernatant were mixed with 50 μl of SDS-PAGE Gel Loading buffer, boiled for about 10 minutes, and then loaded onto the gel (each well contained about 10-30 μl). The remaining sample could be stored at −20° C. for western blots, if necessary. The rest of the supernatant could be stored at −80° C. for further analysis. Centricon and/or Centriprep filters (Amicon) could be used to concentrate the thawed supernatant.

Determination of Molecular Weight of Monodoncin

A 15% polyacrylamide gel with a 5% stacking gel was prepared and electrophoresed to determined the molecular weight of monodoncin (See e.g., Sambrook et al., (1989), Molecular Cloning: A Laboratory Manual, Second Edition (Plainview, N.Y.: Cold Spring Harbor Laboratory Press); Ausubel et al., (1994), Guide to Protein Purification. In Methods in Enzymology, Vol. 182. (J. N. Abelson and M. I. Simon, eds.) Academic Press, San Diego, Calif. As shown in FIG. 9, monodoncin demonstrated a molecular weight of about 5-7 kDa.

Large-Scale Purification of Recombinant Monodoncin

A signal transformed colony was selected by kanamycin, and incubated in 10 ml of BMGY in a 100 ml baffled flask. The cells were grown at 28-30° C. in a shaking incubator (250-300 rpm) until the culture reaches an OD600=2-6 (approximately 16-18 hrs). This 10 ml culture was inoculated in 1 liter of BMGY (Yeast extract 1%, peptone 2%, yeast nitrogen base 1.34%, dextrose 1%, 100 mM potassium phosphate pH 6.0, biotin $4\times10^{-5}$%, and glycerol 1%) in a 2 liter baffled flask and grown at 28-30° C. with vigorous shaking (250-300 rpm) until the culture reaches an OD600=2-6. The cells were harvested by centrifugation at 1500-3000×g for 5 minutes at room temperature. To induce expression, the supernatant was decanted and the cell pellets were resuspended in 1/5 to 1/10 of the original culture volume of BMMY medium (approximately 100-200 ml). The culture was then placed in a 1 liter baffled flask to allow for continuing growth at 28-30° C. with shaking. 100% methanol was added to 0.5% every 24 hours until the optimal time of induction was reached. The cells were then harvested by centrifugation at 1500-3000×g for 5 minutes at room temperature. For intracellular expression, the supernatant was decanted and the cell pellets were stored at −80° C. until ready to process. For secreted protein, the supernatant was saved and chilled to 4° C., and was concentrated by Millipore Pellicon XL. The identical fractions eluted from the preparative column were pooled and finally subjected to the same separation procedure to increase peptide purity. Finally, the fractions containing the monodoncin were lyophilized and kept as dry powder.

EXAMPLE 3

Chemical Synthesis of Monodoncin

Monodoncin was synthesized by the solid-phase synthesis on a Milligen 9050 Pepsynthesizer according to fluoren-9-methyloxycarbonyl (Fmoc)-polypeptide active ester chemistry. (See Tominaga et al. (2001), Pharm. Bull. 49(8):1027-1029).

EXAMPLE 4

Antimicrobial Activity of Monodoncin Against Gram-Negative and Gram-Positive Bacteria and Fungi Bacteria and Culture Condition Monodoncin was tested for its antibacterial activities against various Gram (−) bacteria, including *E. coli, Vibrio harveyi, Vibrio alginolyticus*, and *Salmonella cholesaesuis*, various Gram (+) bacteria, such as *Aerococcus viridian*, and filamentous fungi, such as *Fusarium pisi*.

The bacteria were cultured under conventional methods. For example, *E. coli* strain was cultured in LB, 37° C. The marine microorganisms that are pathogenic for shrimp, such as *Vibrio harveyi* and *Vibrio alginolyticus*, were cultured in trypticase soy broth/agar (1.5% NaCl), 25° C.

Bacteriostatic and Bactericidal Analysis

The minimal inhibitory concentration (MIC) and minimal bactericidal concentration (MBC) were obtained to determine bacteriostatic and bactericidal activities, respectively, for each strain of the bacteria listed above. The MIC was determined by incubating serial dilutions of synthetic antimicrobial peptides and tetracycline with approximately $1 \times 10^8$/ml bacterial colony-forming units in 13×10 mm culture glass tube. The lowest concentration which inhibited bacterial growth was deemed the MIC. The MBC was determined by spreading 100 μl from each tube of the MIC on an LB or TSA plate and incubating overnight. The MBC was indicated by the concentration of synthetic antimicrobial peptides and tetracycline that inhibited growth. Note that, although agar-based assays of antimicrobial activity have been shown to underestimate the antibacterial activity of Gram-negative microorganisms when compared with liquid-based assays, the agar-based assays used in this study quantified remaining viable colonies and not antimicrobial activity.

The bacteriostatic (MIC) and bactericidal (MBC) activities of monodoncin against various Gram (−) and Gram (+) bacteria as well as fungi, as compared to those of penaeidins, were shown in Table 1.

TABLE 1

Bacteriostatic and Bactericidal Activities of Monodoncin and Penaeidins Against Various Gram (+) Bacteria

| Microorganism | Monodoncin | | Penaeidins | |
|---|---|---|---|---|
| | MIC | MBC | MIC | MBC |
| Gram (−) bacteria: | | | | |
| E. coli. | <1 μM | <1 μM | >40 μM | >40 μM |
| Vibrio harveyi | <1 μM | <1 μM | >40 μM | >40 μM |
| Vibrio alginolyticus | <1 μM | <1 μM | >40 μM | >40 μM |
| Salmonella.choleraesuis | 2.4 μM | 4.8 μM | >20 μM | >20 μM |
| Gram (+) bacteria: | | | | |
| Aerococcus viridian | 20 μM | 100 μM | 1.25-2.5 μM | |
| Filamentous fungi: | | | | |
| Fusarium pisi | 5 μM | 20 μM | | |
| Fusarium oxysporum | 10 μM | 20 μM | 5-10 μM | |

The results of Table 1 demonstrate that the bacteriostatic and bactericidal activities of monodoncin was significantly more effective against G (−) bacteria than penaeidins, but was less effective against Gram (+) bacteria than penaeidins. Both monodoncin and penaeidins had similar antimicrobial activities against fungi.

The bacteriostatic and bactericidal activities of the chemical synthetic antimicrobial peptides, including cecropin A, cecropin B, magainins, and pleurocidin, and antibiotic, tetracycline were compared with those of monodoncin on Gram (−) bacteria, including *E. coli* and two *Vibrio* pathogens (Vibrio harveyi and *Vibrio alginolyticus*) by liquid growth inhibition assays. The results (as expressed as minimum inhibiting concentration (MIC) and minimum bactericidal concentration (MBC)) were shown in Table 2.

TABLE 2

Bacteriostatic and Bactericidal Activities of Monodoncin, Cecropin A, Cecropin B, Magainins, Pleurocidin, and Tetracycline Against Various Gram (+) Bacteria

| | Monodoncin | | Cecropin A | | Cecropin B | | Magainins | | Pleurocidin | | Tetracycline | |
|---|---|---|---|---|---|---|---|---|---|---|---|---|
| | MIC | MBC | MIC | MBC | MIC | MBC | MIC | MBC | MIC | MBC | MIC | MBC |
| E. coli | <1 | <1 | 50 | 100 | <50 | 100 | 40 | 70 | 450 | 500 | 3.15 | 403.2 |
| V. harveyi | <1 | <1 | 300 | 400 | 250 | 250 | 30 | 30 | 200 | 200 | 6.3 | 403.2 |
| V. alginolyticus | <1 | <1 | 400 | 450 | 150 | 150 | 150 | 300 | 500 | >500 | 25.2 | >201.6 |

MIC: Minimum inhibiting concentration.
MBC: Minimum bactericidal concentration.
Unit: μM As indicated in Table 2, monodoncin had the smallest MIC and MBC against the tested pathogens, thus demonstrating better bacteriostatic and bactericidal effects than other synthetic antimicrobial peptides and antibiotics.

The bacteriostatic and bactericidal activities of the chemical synthetic antimicrobial peptides, including cecropin A, cecropin B, magainins, and pleurocidin, and antibiotic, tetracycline were compared with those of monodoncin on Gram (+) bacteria, such as *Aerococcus viridian*, and fungi, such as *Fusarium pisi* and *Fusarium oxysporum*. The results are shown in Table 3.

TABLE 3

Bacteriostatic and Bactericidal Activities of Monodoncin, Cecropin A, Cecropin B, Magainins, and Tetracycline Against Gram (+) Bacterium and Fungi

| | Monodoncin | | Cecropin A | | Cecropin B | | Magainins | | Tetracycline | |
|---|---|---|---|---|---|---|---|---|---|---|
| | MIC | MBC | MIC | MBC | MIC | MBC | MIC | MBC | MIC | MBC |
| *Aerococcus viridian* | 20 | 150 | 200 | >500 | 1 | 400 | 1 | 5 | 30 | 300 |
| *Fusarium pisi* | 5 | 20 | 100 | 150 | 20 | 30 | 1 | 1 | 300 | >500 |
| *Fusarium oxysporum* | 10 | 20 | 75 | 150 | 10 | 20 | 1 | 1 | 500 | 500 |

MIC: Minimum inhibiting concentration.
MBC: Minimum bactericidal concentration.
Unit: µM As shown in Table 3, the bacteriostatic and bactericidal activities of monodoncin against Gram (+) bacterium *Aerococcus viridian* were better than cecropin A, cecropin B, and tetracycline but worse than magamins. Same was true against fungi, such as *Fusarium pisi* and *Fusarium oxysporum*.

EXAMPLE 5

Cocktail Therapy of Monodoncin

Monodoncin not only demonstrated bacteriostatic and bactericidal activities on various microorganisms, but also exhibited synergistic effects on antimicrobial activities when it was used together with other conventional antibiotics. This is the so-called "cocktail therapy."

As shown in Table 4, when monodoncin was co-administered with amoxicillin, a penicillin derivative, the MIC and MBC against *Salmonella cholesraesuis*, a Gram (–) bacterium, was significantly lower.

TABLE 4

Bacteriostatic and Bactericidal Activities of Monodoncin in Combination with Amoxicillin Against *Salmonella choleraesuis*

| | Strand 74 | | Strand 75 | |
|---|---|---|---|---|
| | MIC | MBC | MIC | MBC |
| Amoxicillin (A) (µg) | >64 | — | >64 | — |
| Cecropin (µg/ml) | 16.5 | 31.2 | 31.2 | >31.2 |
| Amoxicillin + cecropin (µg/ml) | 8/6.25 | 16/6.25 | >16/6.25 | >16/6.25 |
| Monodoncin (µg/ml) | 16.5 | 31.2 | 16.5 | 31.2 |
| Amoxicillin + monodoncin (µg/ml) | 8/1.95 | 16/3.9 | 8/1.95 | 16/6.25 |

As shown in Table 4, amoxicillin itself did not have bactericidal activity against *S. choleraesuis*. Cecropin alone, however, had demonstrated bacteriostatic and bactericidal activities against *S. choleraesuis*, similar to those of monodoncin. However, the combined usage of amoxicillin and monodoncin gave rise to far better bacteriostatic and bactericidal activities than the combined use of amoxicillin and cecropin, demonstrating that monodoncin provided far much better synergistic effects on antimicrobial activity than cecropin and was suitable for use in a "cocktail therapy." This result, in combination with the results shown in Tables 1-3, further demonstrated that monodoncin could be use to treat infection in humans and animals, because many of the bacteria that could be inhibited (i.e., bacteriostatic) and killed (i.e., bactericidal) were pathogens to humans and animals.

EXAMPLE 6

Inducibility of Monodoncin by Immuno-Challenges

The expression of monodoncin expression in response to microbial challenge was also tested.

Immuno-Challenge

*Vibrio harveyi* is a gram-negative marine bacterium that is in the natural living environment of the tiger shrimp. A suspension of the microorganism 50 ml containing $10^5$ cells was used for each tiger shrimp. The suspension was injected into the shrimp abdominal muscle. Hemocytes were collected as Example 1 at different times (from 0 to 72 hours) post-injection. Unchallenged animals were used as controls.

In two independent experiments, hemolymph was collected at 0, 3, 6, 12, 24, 48 and 72 hours post-injection, and total RNA was extracted from circulating hemocytes. Three animals were punctured at every time and individual shrimp hemocytes were treated separately. The 4 µg total RNA were analyzed by semi-quantitative RT-PCR and for every shrimp. The STORM™ quantified monodoncin and β-actin hybridization signals were compared for every animal, and the individual data were grouped together at each time post-injection. Mean values at each time were used to determine the monodoncin:β-actin signal ratio ($P>0.05$).

FIG. 4 shows a time-course analysis of monodoncin expression in hemocytes after immuno-challenge. After *Vibrio harveyi* challenge, the semi-quantitative RT-PCR was performed on 4 µg total RNA extracted from shrimp hemocytes at different time intervals after challenge. The experiments were individually analyzed for 3 animals at each time. For every animal, the signals obtained with monodoncin Dig-labeled probe were quantified by the STORM™ system and compared to those obtained with the β-actin specific probe. Mean values at each time were used to determine the monodoncin:β-actin signal ratio (p>0.05) and plotted. Results shown were the mean of two independent experiments. The expression level in unchallenged shrimp was normalized to 1 and results were given as expression relative to this level.

Data analysis revealed a little decrease in monodoncin mRNA levels at 3 hours post-injection. Such a decrease in monodoncin mRNA level could be associated with a partial decrease of monodoncin-producing hemocytes. Return to control levels was observed after 12 hours and a slight increase was noticed at 24 hours. The expression levels at 48 and 72 hour were return to the control levels and the mRNA level of monodoncin was not significantly changed in this experiment. These results were obtained for two experiments independently performed, and even though they did not give precise information in terms of gene regulation, they clearly indicated that monodoncin synthesis in hemocytes was not enhanced by *Vibrio harveyi* injection.

On the other hand, the microbial challenge could also lead to a decrease in monodoncin gene transcription subsequent to degranulation events and release of the peptides into the blood. Thereafter, the amount of monodoncin was returned to the control levels after 12 hours and a slight increase was noticed at 24 hours. The expression levels at 48 and 72 hour were return to control levels and the mRNA level of monodoncin was not significantly changed in this experiment. Even though they did not give precise information in terms of gene regulation, they clearly indicated that monodoncin synthesis in hemocytes was not enhanced by *Vibrio harveyi* injection. The results demonstrate that monodoncin did not belong to the inducible antimicrobial peptides such as that found in insects and that it could be constitutively expressed in hemocytes of black tiger shrimp.

As shown in FIG. 5, the mortality rate of the tiger shrimp was reduced to 40% of that in the untreated group, which suggested that monodoncin was effective as an antimicrobial agent in treating aquatic species for pathogen infections. This result immediately suggest a possible oral delivery or an injection therapeutic administration method for inhibiting pathogen infections.

EXAMPLE 7

EM and AFM Analysis of Interactions of Monodoncin and Pathogen Membrane

Monodoncin at 10 μm was used to treat *E. Coli* and *Vibrios*, and the pathogens prior to and after the treatment were monitored under Scanning Electron Microscope (SEM) and Atomic Force Microscope (AFM).

AFM Method

A 3-ml culture of *V. harveyi* or *E. coli* was grown in a medium overnight at 25° C. The culture was freshly prepared for AFM assay on that day. A 1 ml culture of the bacterium was centrifuged at 1500×g for 10 minutes at room temperature and washed with dH$_2$O. The medium was decanted and the bacteria were resuspended in 1 ml of dH$_2$O. The 900 μl control sample contained bacteria that were treated without adding 1 μl of 1 mM monodoncin. About 100 μl of each sample were manually spread onto a polished microscope glass slide to create a bacterial film, which was rapidly fixed by air drying. The atomic force microscopy (AFM) was performed in air on the bacterial film using an AFM (Explorer model, TopoMetrix, Santa Clara, Calif.) in contact mode. The glass slide carrying the bacterial film was scanned by AFM, and the integral camera was used to locate the regions of interest. Contact mode silicon tips with a spring constant of ~0.3 newtons/m were used. The force applied to the sample during imaging was typically 15 nanonewtons. Repeated scanning of the same sample confirmed that no physical damage occurred during AFM. AFM images were processed and analyzed using the software SPMLab Version 4.0 (TopoMetrix).

SEM Method:

Scanning electron microscopy (SEM) was conducted by incubating 50 ml of *E. coli* (109 C.F.U./ml) with or without 50 μl monodoncin (10000 μM) at 37° C. for 1 h, 3 h, 6 h, and 12 h. Three milliliters of each of the bacterial suspensions (at various time frames) were fixed by adding 1 ml of 6% glutaraldehyde in 0.1 M sodium cacodylate trihydrate buffer (pH 6.8). After fixation for 1 h at 48° C., the bacterial suspensions were pelleted, the used fixative was removed, 2 ml of the new fixative were added, and the bacteria were incubated for 5 min at 48° C. Two additional 5-min fixations were conducted, followed by addition of 2 ml of 1% osmium tetroxide in 0.1 M cacodylate buffer, and the fixation was allowed to proceed for 30 min at 48° C. The osmium tetroxide was removed, and the bacterial suspensions were washed in 2 ml of 0.1 M cacodylate buffer. After 18 h of incubation at 48° C. in cacodylate buffer, the bacterial suspensions were washed three times with double-distilled water, and about 150 μl of the suspension were mounted onto poly-L-lysine-coated coverslips. After 2 h, the bacteria on the coverslips were dehydrated by using a series of ethanol washes, rinsed in hexamethyldisilazone, and mounted onto aluminum SEM mounts (Ebtac, Agawan, Mass.). The SEM mounts were then sputter coated with gold (Edwards S150A sputter coater; Edwards High Vacuum, Crawley, West Sussex, England) and analyzed on a Hitachi H300-3010 scanning image accessory electron microscope.

FIG. 6 A-D demonstrate the interaction of monodoncin with *E. coli* (at 15,000×) under SEM. The bright spot (hole) started to show on the surface of the bacterium after 3 hrs of monodoncin treatment (FIG. 6 A-B). At 6 hrs of treatment, some bacteria exhibited several holes on the surface (FIG. 6C). At 12 hrs, the number of bacteria in the culture was significantly reduced, demonstrating the lyses of bacteria.

Figure 8:
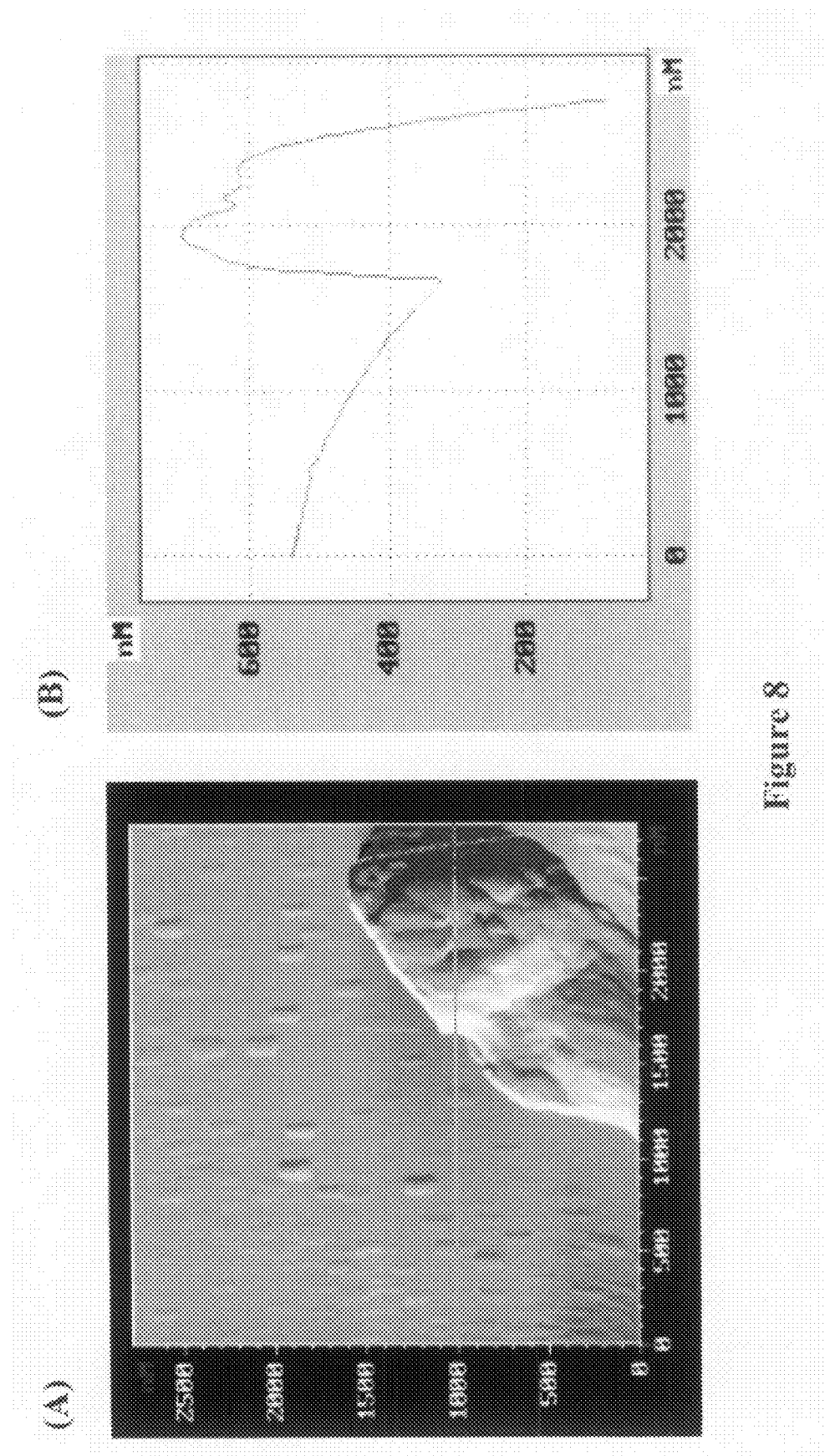

FIGS. 7 and 8 are micrographs of monodoncin after being interacted with *E. coli* (FIG. 7) and *V. harveyi* (FIG. 8). The AFM micrographs show that holes were formed on the surface of the microorganisms, which are about 50-60 nm in diameter (FIG. 8B).

EXAMPLE 8

In Vivo Gene Transfer of Monodoncin to Other Crustacean

Electroporation Mediated Gene Transfer and In Vivo Spermatophore-Mediated Gene Transfer The Baekon 2000 system (Baekon Co., CA) or BTX (San Diego, Calif.). ElectroSquarePorator T820 mode were used to transfer foreign DNA into fertilized shrimp eggs. The Baekon system was chosen because of its ease of operation and improved electrode configuration which allowed for rapid gene transfer. Optimal conditions for electroporation were standardized using 50 eggs, 20 μg CMV-monodoncin cDNA or CMV-cecropin cDNA fragments, and shrimp saline solution as the electroporation medium. For in vivo style electrode (BTX 2 Needle Array Electrode), specially designed for shrimp spermatophore gene deliver, the following settings were found to provide optimal electroporation results with the Baekon apparatus: amplitude 3.0 kv; pulse frequency $2^6$; burst time 0.4 S; cycle number 5; pulse width 160 μS; and distance of electrode from surface of buffer 1 mm. This method of gene transfer is referred to as sperm-mediated gene transfer (SMGT).

Classical approaches for producing transgenic animal require labor-intensive, time-consuming, and expensive methods with low efficiency of transgenic production. Here, a promising approach for mass producing transgenic animals was achieved by using an in vivo spermatophore-mediated gene transfer in Penaeid shrimp.

Figure 10A:
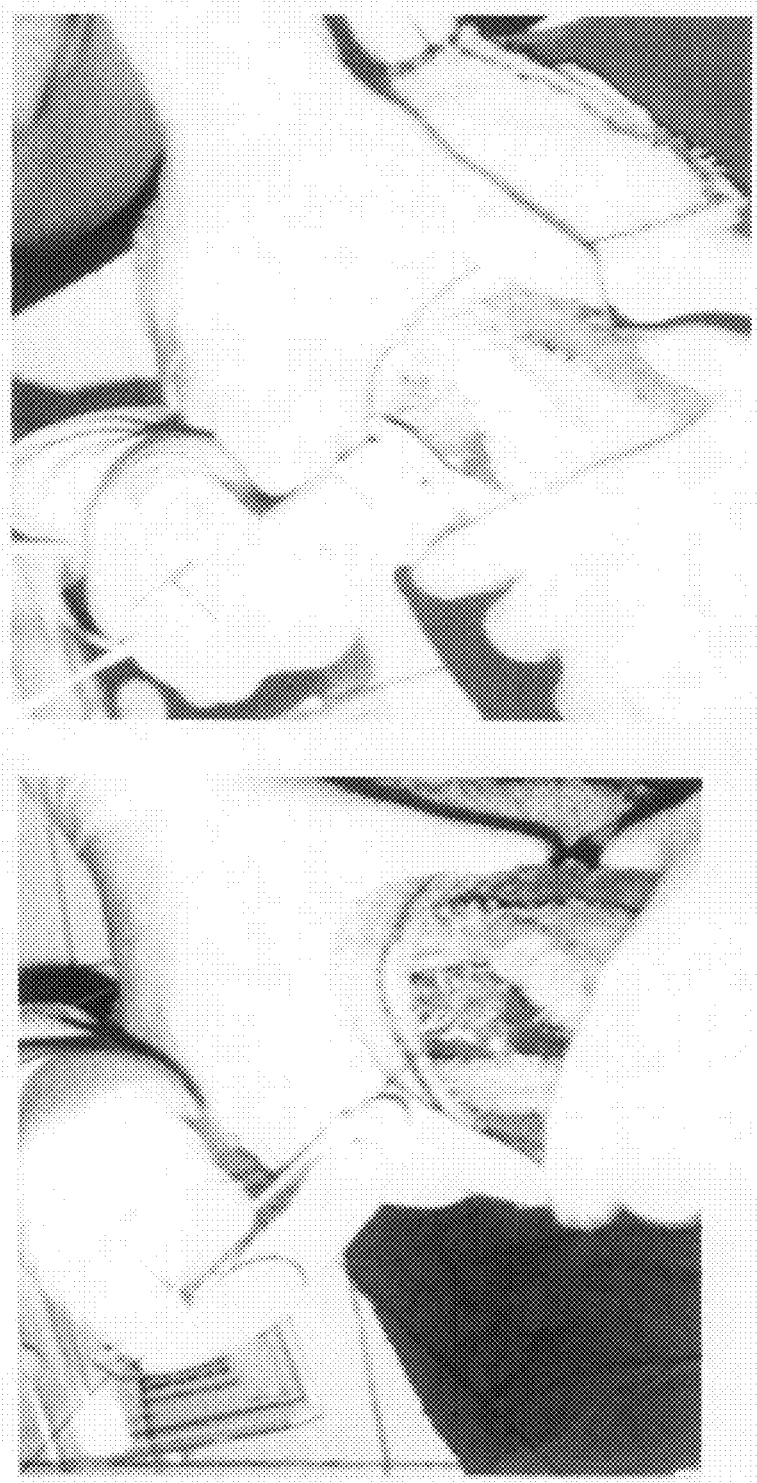

To eliminate the handling stress and reuse broods, a electroporation-based gene transfer method or an in vivo electroporation-mediated gene transfer method was developed to deliver the antimicrobial peptide transgene into the high economic commercial penaeid species, such as tiger shrimp (*Penaeus monodon*) and white shrimp (*Lipopenaeus vannamei*). As shown in FIG. 10, a spermatophore-mediated gene transfer (SMGT) method was developed, which involved the injection of the transgene solution into the spermatophores of thelycum of female tiger shrimp (FIG. 10A) or the spermatophore of male of *P vannamei* (FIG. 10B), followed by the insertion of BTX 2-Needle array into the spermatophore and proceeded with electroporation at amplitude 1.0~1.5 kv; pulse frequency $2^3$; burst time 0.4 S; cycle number 4; pulse width 90 μS.

After treatment, the electroporated brood of tiger shrimp were cultured in spawning tank until spawning. The electroporation treated *P vannamei* were proceeded with artificial insemination and maintained at the spawning tank until spawning. The fertilized shrimp eggs were collected for further incubation. Between 29% to 80% of the hatched fry were found to carry the AMP transgene by PCR analysis. Several $P_1$ AMP transgenic *P vannamei* exhibited significant disease resistant of *vibrio* pathogene infection compared to non-transgenic controls.

EXAMPLE 9

Amino Acid Sequence Comparison Between Monodoncin and Penaeidins

To determine the amino acid homology between monodoncin and other shrimp AMPs, a comparison of the amino acid sequences between monodoncin and the AMPs of the other shrimp AMPs (i.e., penaeidin isoforms) based on currently available nucleic acid and protein databases of published shrimp AMPs was performed. The results showed that the full length of monodoncin peptide from tiger shrimp shared a homology of only about 24% to 51% of the penaeidin isoforms from *Litopenaeus vannamei*. (Table 5).

TABLE 5

% Homology of amino acids of full length Monodoncin and Penaeidin isoform peptides

|  | penaeidin-1 | penaeidin-2 | penaeidin-3a | penaeidin-3b | penaeidin-3c |
|---|---|---|---|---|---|
| Monodoncin | 24% | 44% | 50% | 50% | 51% |

The % of homology of the amino acids between the mature peptide of monodoncin and those of penaeidin isoforms was about 46%-54%. (Table 6).

TABLE 6

% Homology of Amino Acids of the Mature Peptide of Monodoncin and Penaeidin Isoforms

|  | penaeidin-1 | penaeidin-2 | penaeidin-3a | penaeidin-3b | penaeidin-3c |
|---|---|---|---|---|---|
| Monodoncin | 46% | 45% | 53% | 53% | 54% |

A comparison of the amino acid sequences between the mature peptide of monodoncin and the mature peptides of the penaeidin isoforms was shown in FIG. 2.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

We claim:

1. An isolated polynucleotide, comprising the nucleic acid sequence of SEQ ID NO: 4.

2. The isolated polynucleotide of claim 1, wherein said polynucleotide comprising the nucleic acid sequence of SEQ ID NO:3.

3. A recombinant construct comprises a nucleic acid sequence according to claim 1 and a vector.

4. The recombinant construct according to claim 3, wherein said vector is a plasmid or a viral carrier.

5. The recombinant construct according to claim 3, wherein said recombinant construct is expressed in a host.

6. The recombinant construct according to claim 5, wherein said host is yeast.

7. An isolated polynucleotide comprising a nucleic acid sequence of SEQ ID NO:2, which encodes an antimicrobial peptide having an amino acid sequence of SEQ ID NO:1.

8. The isolated polynucleotide according to claim 7, wherein said polynucleotide is reversely transcribed from an mRNA which is isolated from tiger shrimp (*Penaeus monodon*).

* * * * *

SEQUENCE LISTING

```
<160> NUMBER OF SEQ ID NOS: 13

<210> SEQ ID NO 1
<211> LENGTH: 74
<212> TYPE: PRT
<213> ORGANISM: Penaeus monodon

<400> SEQUENCE: 1

Met Arg Leu Val Val Cys Leu Val Phe Leu Ala Ser Phe Ala Leu Val
1               5                   10                  15

Cys Gln Ala Gln Gly Tyr Gln Gly Gly Tyr Thr Arg Pro Phe Pro Arg
            20                  25                  30
```

```
Pro Pro Tyr Gly Gly Tyr His Pro Val Pro Val Cys Thr Ser Cys
        35              40                  45

His Arg Leu Ser Pro Leu Gln Ala Arg Ala Cys Cys Arg Gln Leu Gly
 50              55                  60

Arg Cys Cys Asp Ala Lys Gln Thr Tyr Gly
 65                  70
```

<210> SEQ ID NO 2
<211> LENGTH: 1363
<212> TYPE: DNA
<213> ORGANISM: Penaeus monodon
<220> FEATURE:
<221> NAME/KEY: misc_feature
<222> LOCATION: (819)..(819)
<223> OTHER INFORMATION: n = a, c, g, or t

<400> SEQUENCE: 2

```
accagtcggt gcttggctct cacctgaccc ccacctgtag agtccgagac gtcttgcccg    60
ggttccttcc tgtgcctgcc atgcgtctcg tggtctgcct ggtcttcctg gcctccttcg   120
ccctggtctg ccaagcccaa gggtaccagg gtggttacac acgcccgttc cccagaccac   180
cctatggggg aggatatcat ccagttcctg gtaaagtttc taaaggttat ttgttggtct   240
atatggtaat cgtattattg tcaccaatca catcatattg ttattagtaa tcgctaacat   300
tatttgcatt ccatatttat tactattact gaatatctct attccttcaa tacaactatt   360
cattctgtgt taaaaaatgt atatagttta ttgttagtat tgacaacatt taaaagagat   420
gcagatgata ctcgtaaaag agaaagaaag aaaaaaaacat aatgatgatt aataatgata   480
gctttaatga taaccatgag tctactgtct taccaataat aaggtcatgt attaatcagg   540
tgatagttgt aatgtatatt atagttataa aaacactcgt ggtgacaata acaagtggcc   600
aaaactagaa ttataaaatgc agacattatt atataatagt ataagaata acaccaataa   660
tactaacgag aataatgatt gcaccaatag aggtgatact gataatgaaa ataatcttaa   720
tagccgtact catggcaatg atagggcact gataatgata attatcggtc acagattcta   780
cactaataat aatgaatggg atactaaaga tgatactant attaatggta atgaagcgaa   840
atataccaaa aatttcgcaa atctctaaat attttttattt tccttcccag tttgcacttc   900
atgccacagg cttagcccct acaagctcg tgcttgctgc aggcagttag gacgttgttg   960
tgatgcaaag caaacatatg gttgatggag aagacaacga aaaactgact gacttcacaa  1020
tgtattaatc agttgtgaag aaagtgcaac cctgattttg aactgtattt tctagttcca  1080
ttttcttact tttgcttgtg gaaaggatgt aggtatttgg attttccatg aatgtatgat  1140
gaatgaaagt gcatgtggga tgtatgtgca tacagtcgta tttgtcccag caggtcctcg  1200
tgtattcaca ggagaaagat atcgtgttgt ttgactttcg ttgtagttat ttgtaggtat  1260
gggtctgtgt gtggttggtg tttgcatatt tcccaaagga cattcggaat tgtactactc  1320
ttttacaaat aaaattgata tctgtgaaaa aaaaaaaaaa aaa                    1363
```

<210> SEQ ID NO 3
<211> LENGTH: 225
<212> TYPE: DNA
<213> ORGANISM: Penaeus monodon

<400> SEQUENCE: 3

```
atgcgtctcg tggtctgcct ggtcttcctg gcctccttcg ccctggtctg ccaagcccaa    60
gggtaccagg gtggttacac acgcccgttc cccagaccac cctatggggg aggatatcat   120
```

-continued

```
ccagttcctg tttgcacttc atgccacagg cttagcccct tacaagctcg tgcttgctgc    180
aggcagttag gacgttgttg tgatgcaaag caaacatatg gttga                   225
```

<210> SEQ ID NO 4
<211> LENGTH: 168
<212> TYPE: DNA
<213> ORGANISM: Penaus monodon

<400> SEQUENCE: 4

```
caagggtacc agggtggtta cacacgcccg ttccccagac caccctatgg gggaggatat    60
catccagttc ctgttttgcac ttcatgccac aggcttagcc ccttacaagc tcgtgcttgc   120
tgcaggcagt taggacgttg ttgtgatgca aagcaaacat atggttga                 168
```

<210> SEQ ID NO 5
<211> LENGTH: 21
<212> TYPE: DNA
<213> ORGANISM: artificial sequence
<220> FEATURE:
<223> OTHER INFORMATION: primer MP-1

<400> SEQUENCE: 5

```
gtctgccaag cccaagggta c                                              21
```

<210> SEQ ID NO 6
<211> LENGTH: 21
<212> TYPE: DNA
<213> ORGANISM: artificial sequence
<220> FEATURE:
<223> OTHER INFORMATION: primer MP-2

<400> SEQUENCE: 6

```
ctgcctgcag caagcacgag c                                              21
```

<210> SEQ ID NO 7
<211> LENGTH: 27
<212> TYPE: DNA
<213> ORGANISM: artificial sequence
<220> FEATURE:
<223> OTHER INFORMATION: primer Ps-2

<400> SEQUENCE: 7

```
cagggtggtt acacacgccc gttcccc                                        27
```

<210> SEQ ID NO 8
<211> LENGTH: 27
<212> TYPE: DNA
<213> ORGANISM: artificial sequence
<220> FEATURE:
<223> OTHER INFORMATION: primer Ps-2

<400> SEQUENCE: 8

```
gcagcaagca cgagcttgta agggct                                         27
```

<210> SEQ ID NO 9
<211> LENGTH: 37
<212> TYPE: DNA
<213> ORGANISM: artificial sequence
<220> FEATURE:
<223> OTHER INFORMATION: adaptor primer

<400> SEQUENCE: 9

```
ggccacgcgt cgactagtac tttttttttt ttttttt                             37
```

```
<210> SEQ ID NO 10
<211> LENGTH: 20
<212> TYPE: DNA
<213> ORGANISM: artificial sequence
<220> FEATURE:
<223> OTHER INFORMATION: amplification primer

<400> SEQUENCE: 10
ggccacgcgt cgactagtac                                              20

<210> SEQ ID NO 11
<211> LENGTH: 36
<212> TYPE: DNA
<213> ORGANISM: artificial sequence
<220> FEATURE:
<223> OTHER INFORMATION: anchor primer
<220> FEATURE:
<221> NAME/KEY: misc_feature
<222> LOCATION: (24)..(35)
<223> OTHER INFORMATION: n = inosine

<400> SEQUENCE: 11
ggccacgcgt cgactagtac gggnngggnn gggnng                            36

<210> SEQ ID NO 12
<211> LENGTH: 27
<212> TYPE: DNA
<213> ORGANISM: artificial sequence
<220> FEATURE:
<223> OTHER INFORMATION: anti-sense primer MP-2

<400> SEQUENCE: 12
cggccgtcaa ccatatgttt gctttgc                                      27

<210> SEQ ID NO 13
<211> LENGTH: 30
<212> TYPE: DNA
<213> ORGANISM: artificial sequence
<220> FEATURE:
<223> OTHER INFORMATION: sense primer MP-1

<400> SEQUENCE: 13
gaattccaag ggtaccaggg tggttacaca                                   30
```